(12) United States Patent
Doyle et al.

(10) Patent No.: US 8,821,453 B2
(45) Date of Patent: Sep. 2, 2014

(54) FOLDING PANEL NEEDLE GUARD

(75) Inventors: Mark Christopher Doyle, Del Mar, CA (US); Philip E. Dowds, San Diego, CA (US); James M Verespej, San Marcos, CA (US); Frederic P. Field, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 241 days.

(21) Appl. No.: 13/189,704

(22) Filed: Jul. 25, 2011

(65) Prior Publication Data

US 2013/0030376 A1 Jan. 31, 2013

(51) Int. Cl.
*A61M 5/32* (2006.01)
*A61M 5/00* (2006.01)

(52) U.S. Cl.
USPC ............ 604/197; 604/198; 604/192; 604/263

(58) Field of Classification Search
USPC .......... 604/192, 198, 110, 263, 136, 137, 197
See application file for complete search history.

(56) References Cited

U.S. PATENT DOCUMENTS

| | | |
|---|---|---|
| 4,735,618 A | 4/1988 | Hagen |
| 4,790,828 A * | 12/1988 | Dombrowski et al. ........ 604/198 |
| 4,935,013 A | 6/1990 | Haber et al. |
| 4,950,250 A * | 8/1990 | Haber et al. ................... 604/192 |
| 5,078,697 A | 1/1992 | Rammler |
| 5,250,031 A | 10/1993 | Kaplan et al. |
| 5,295,972 A | 3/1994 | Mischenko |
| 5,304,151 A | 4/1994 | Kuracina |
| 5,348,544 A | 9/1994 | Sweeney et al. |
| 5,368,568 A | 11/1994 | Pitts et al. |
| 5,487,733 A | 1/1996 | Caizza et al. |
| 5,512,050 A | 4/1996 | Caizza et al. |
| 5,531,704 A | 7/1996 | Knotek |
| 5,591,133 A | 1/1997 | Feuerborn et al. |
| 5,980,488 A | 11/1999 | Thorne |
| 6,171,284 B1 | 1/2001 | Kao et al. |
| 6,254,575 B1 | 7/2001 | Thorne, Jr. et al. |
| 6,261,264 B1 | 7/2001 | Tamaro |
| 6,409,706 B1 | 6/2002 | Loy |
| 6,972,002 B2 | 12/2005 | Thorne |
| 6,986,759 B1 | 1/2006 | Jeremijevic |
| 7,211,069 B2 | 5/2007 | Lehmann |
| 7,300,423 B2 | 11/2007 | Cocker et al. |
| 7,922,698 B2 | 4/2011 | Riesenberger et al. |
| 2009/0082734 A1 | 3/2009 | Walters et al. |
| 2009/0171285 A1 | 7/2009 | Wang |
| 2010/0298739 A1 | 11/2010 | Steube et al. |

FOREIGN PATENT DOCUMENTS

| | | |
|---|---|---|
| EP | 0344606 B1 | 12/1993 |
| EP | 0470228 B1 | 11/1995 |
| EP | 1592472 B1 | 1/2007 |
| EP | 2027879 A1 | 2/2009 |

(Continued)

*Primary Examiner* — Bhisma Mehta
*Assistant Examiner* — Bradley G Thomas, Jr.
(74) *Attorney, Agent, or Firm* — One LLP

(57) ABSTRACT

A folding panel needle guard comprises front and rear panels coupled together at hinges, a collar attached to the front panels at hinges, a guard base element coupled to the rear panels at hinges, a hub and a spring to unfold and lock the front and rear panels in a co-linear needle shielded configuration. The folding panel needle guard is mountable to a needle or syringe assembly.

15 Claims, 46 Drawing Sheets

(56) References Cited

FOREIGN PATENT DOCUMENTS

| | | | |
|---|---|---|---|
| GB | 2301036 A | 11/1996 | |
| GB | 2369779 A | 6/2002 | |
| NL | 9001664 A | 2/1992 | |
| WO | WO 93/17732 A2 | 9/1993 | |
| WO | WO 93/17735 A2 | 9/1993 | |
| WO | WO 94/19036 A1 | 9/1994 | |
| WO | WO 01/28611 A2 | 4/2001 | |
| WO | WO 01/36030 A1 | 5/2001 | |
| WO | WO 2006/032064 A1 | 3/2006 | |
| WO | WO 2010/046112 A1 | 4/2010 | |
| WO | PCT/US2012/048023 | 9/2012 | |

* cited by examiner

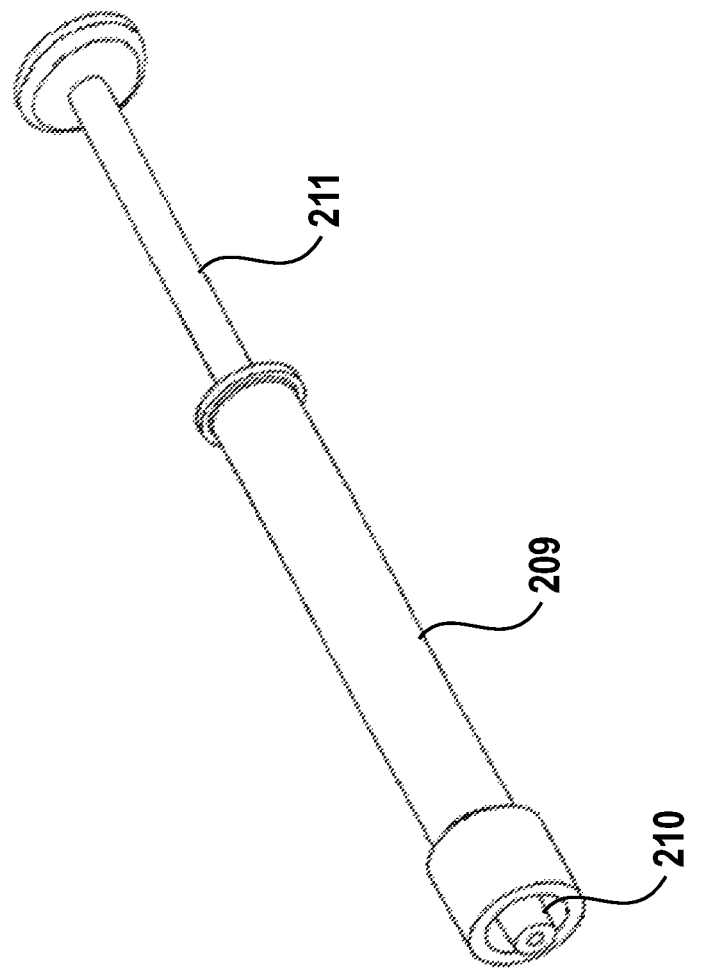
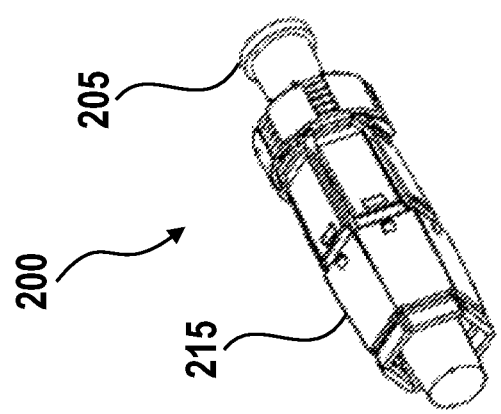
FIG. 21

FOLDING PANEL NEEDLE GUARD

FIELD

The embodiments provided herein relate generally to safety systems for syringes, and more particularly to a needle guard for a syringe that includes an automatically activated shield for covering a needle of the syringe.

BACKGROUND INFORMATION

Medication is often dispensed using a medicine cartridge, such as a glass syringe, having a barrel with a needle at one end and a plunger slidably inserted into the other end and coupled to a rubber stopper. Such cartridges are often referred to as "pre-filled syringes" because they may contain a specific dosage or volume medication when they are initially provided, as compared to conventional syringes that are furnished empty and filled by the user before making an injection.

The glass syringe and rubber stopper have, for years, provided an ideal drug storage closure having unique properties of impermeability to oxygen, low extractables, biocompatibility, durability, etc. However, they are both formed by processes that do not lend themselves to tight geometrical tolerances. Tight tolerances were not originally needed by these devices because they were not used mechanically with other devices.

Due to the risk of communicable diseases, a number of syringes and adapters have been developed that are intended to prevent accidental needle sticks and/or inadvertent reuse of a syringe. Conventional passive anti-needle stick safety devices for prefilled syringes must mount to the syringe but not interfere excessively with the force required to move the plunger rod during injection nor prevent the full travel of the plunger rod. The safety mechanism necessarily must be triggered toward the end of administration of the drug (near the end of the plunger rod travel). However, since virtually all safety devices locate the syringe against the safety device at a point under the syringe finger flange, the operability of the safety device tends to be dependent on the tolerances of the syringe and stopper.

In addition, because conventional passive anti-needle stick safety devices for prefilled syringes tend to mount to or on the barrel of the syringe, the safety devices tend to obscure the contents of the syringe and must be applied post filling of the syringe.

Prefilled syringes tend to be shipped to pharma customers as ready-to-fill syringes, which are ones that have been thoroughly cleaned inside and outside after the forming processes and attachment of a needle and then placed in sealed tubs that are then sterilized and shipped to the pharma customers ready for filling with a medicine. The syringe tubs may contain 100 to 160 syringes each with a geometrical spacing and access that is consistent with established syringe handling equipment. A safety device applied to the syringe must not obscure the optical inspection systems that are in place to check the syringes prior to filling them with medication.

Accordingly, it would be desirable to have a needle guard for a syringe having the safety device triggering mechanism independent of the syringe geometry and that assembles to the syringe without adversely affecting the syringe position with respect to the syringe handling tub or the way the handling equipment conveys the syringes during filling and packaging nor impedes the inspection processes.

SUMMARY

The systems and methods described herein are directed to a needle guard for a syringe having the safety device triggering mechanism independent of the syringe geometry. In one embodiment, a folding panel needle guard comprises front and rear panels coupled together at hinges, a collar attached to the front panels at hinges, a guard base element coupled to the rear panels at hinges, a hub and a spring to unfold and lock the front and rear panels in a co-linear needle shielded configuration. The folding panel needle guard is mountable to a needle or syringe assembly.

In another embodiment, the folding panel needle guard includes a control ring operably coupled to the spring and positionable over the hinges between the front and rear panels to lock the front and rear panels in a co-linear needle shielded configuration.

In operation, the needle is inserted into a patient to complete an injection, collapsing the folding panel needle guard and causing the release of the spring. Upon withdrawal of the needle from the patient, the spring biases the rear and front panels to unfold and then locks the front and rear panels in a co-linear needle shielded configuration.

Other systems, methods, features and advantages of the invention will be or will become apparent to one with skill in the art upon examination of the following figures and detailed description.

BRIEF DESCRIPTION OF THE FIGURES

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIG. 11B depicts a detail view from FIG. 11A shown partially from underneath showing the relative positions of the control ring and latch arm and the interference there between.

FIG. 21 depicts a partial exploded perspective view showing an external syringe with an external Luer connector adapted to connect to the Luer connector of the needle assembly.

FIG. 27B depicts a detail view from FIG. 27A shown partially from underneath showing the relative positions of the control ring and latch arm and the interference there between.

DETAILED DESCRIPTION

Figure 1:
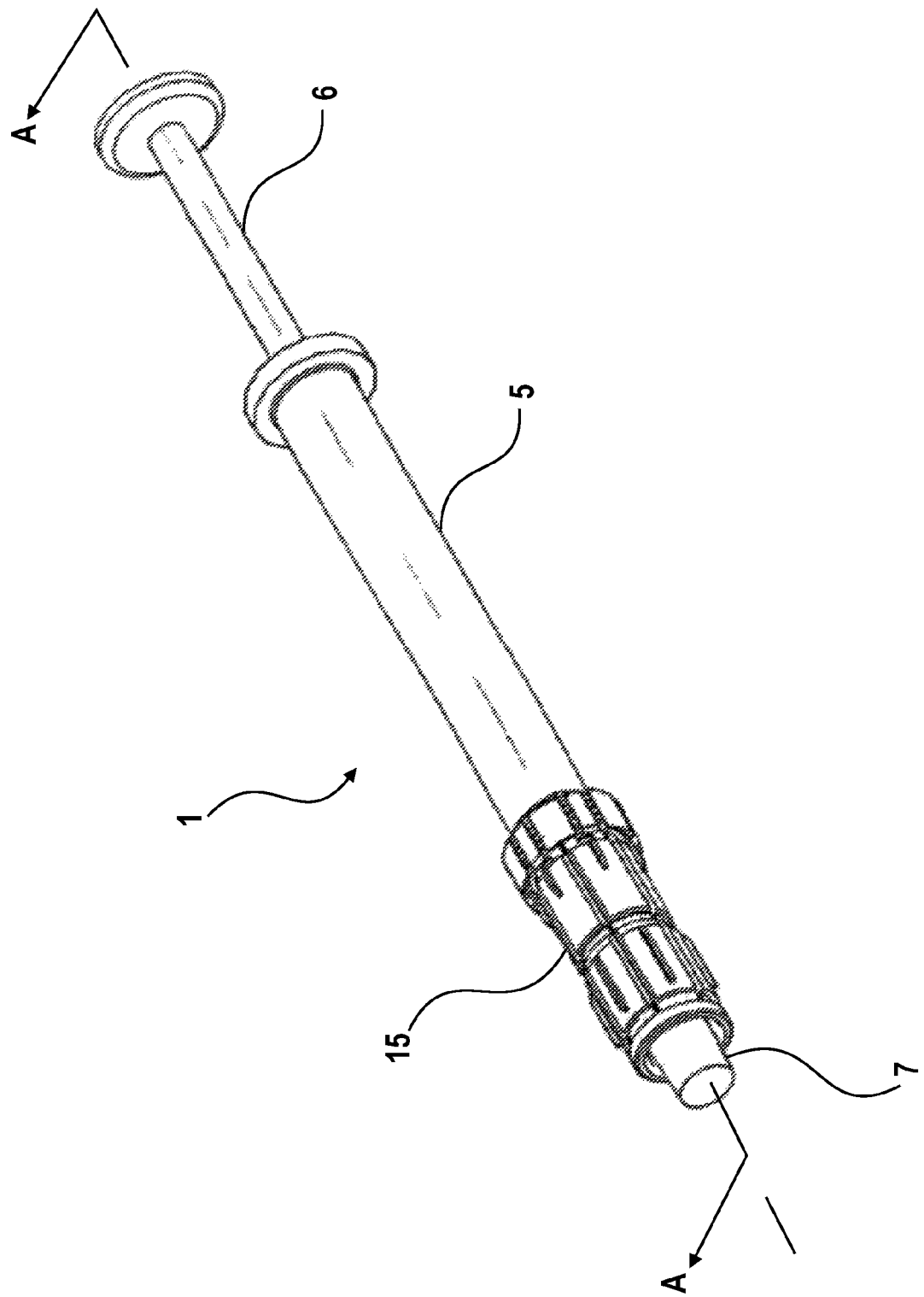
FIG. 1 depicts a perspective view of a syringe assembly comprising a syringe, protective cap, and an embodiment of a folding panel needle guard coupled to the syringe.
Figure 2:
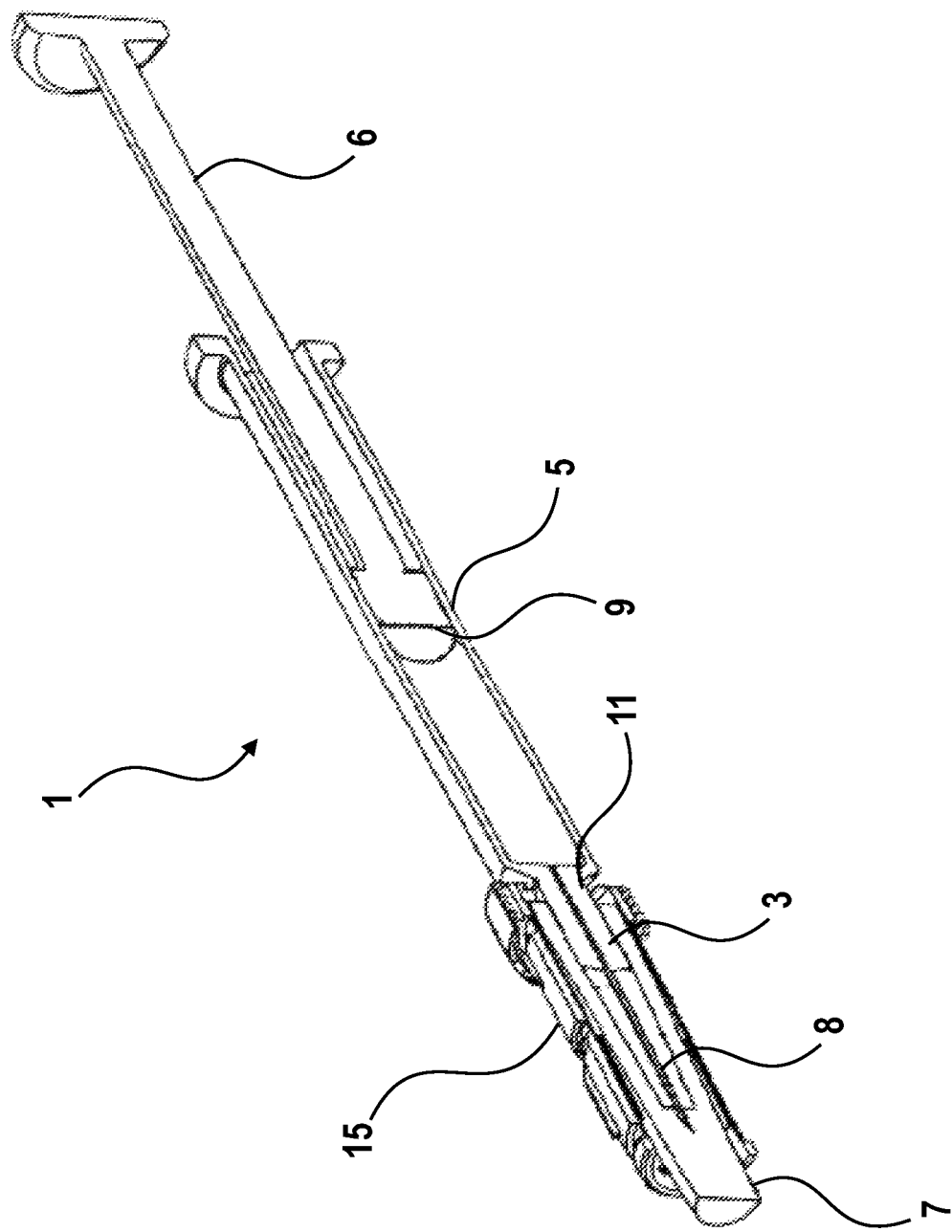
FIG. 2 depicts a sectional perspective view of the syringe assembly taken along line A-A in FIG. 1.

The systems and methods described herein are directed to a needle guard for a syringe having the safety device triggering mechanism independent of the syringe geometry. Turning now to the figures, FIGS. 1-8B show one embodiment of a folding panel needle guard. As depicted in FIGS. 1 and 2, a syringe assembly 1 comprises a syringe 5, a protective cap 7 positioned over a needle 8, and a folding panel needle guard 15. The syringe 5 includes a plunger 6 with a rubber stopper 9 on its distal end slidably received in the syringe 5 from a proximal end. The needle 8, shown as a staked needle, extends from a needle hub 3 at a distal end of the syringe 5. The folding panel needle guard 15 is shown coupled to the syringe 5 at an annular recess 11 (shown in detail in FIG. 6A) formed in the needle hub 3. As discussed in detail below in regard to FIGS. 4-8B, the folding panel needle guard 15 comprises front and rear panels 18 and 22 coupled together at hinges 21, a collar 24 attached to the front panels 18 at hinges 20, a guard base element 17 coupled to the rear panels 22 at hinges 23, a hub 30 and a spring 34 to unfold and lock the front and rear panels 18 and 22 in a substantially co-linear needle shielded configuration.

Figure 3:
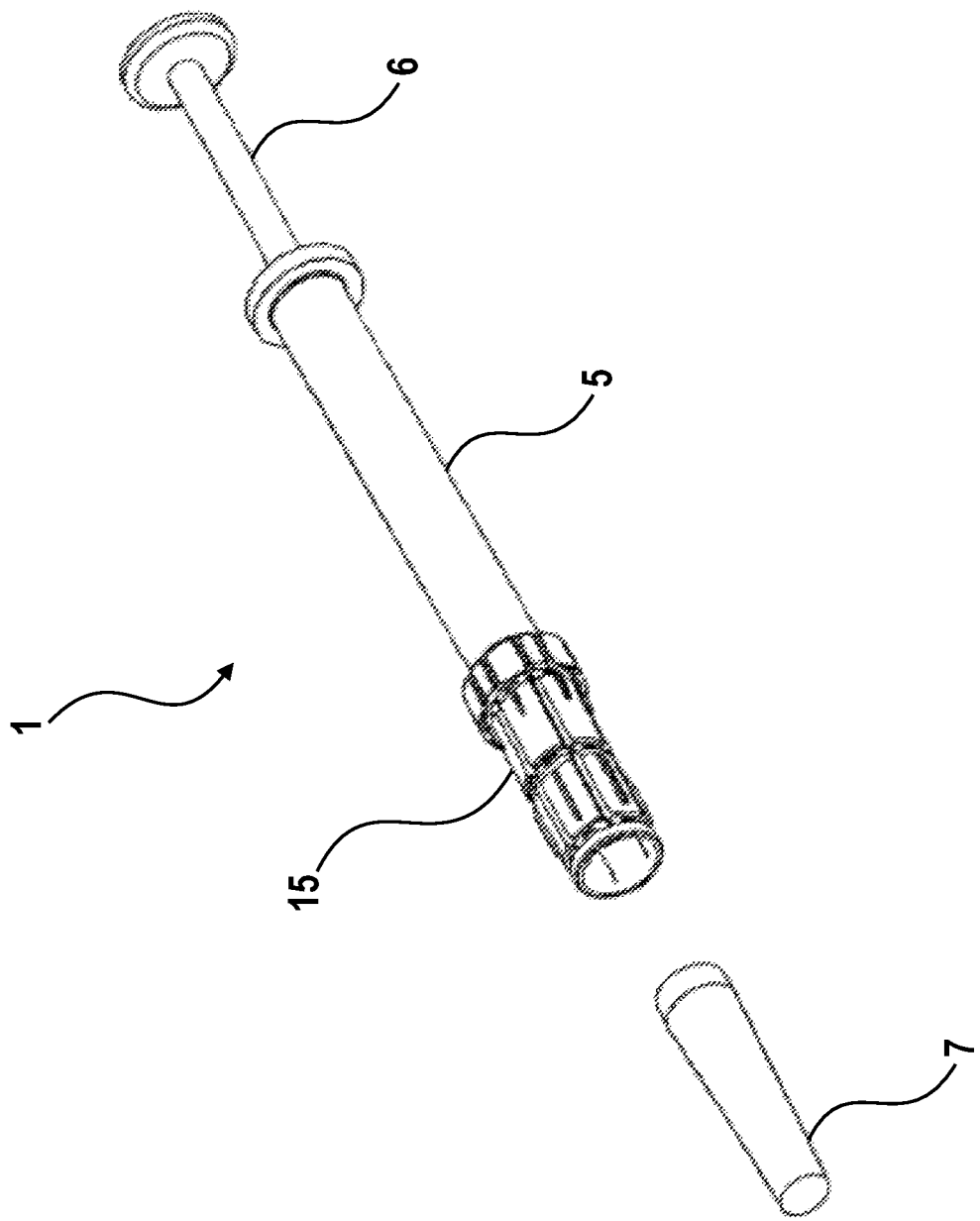
FIG. 3 depicts a partially exploded perspective view of the syringe assembly in FIG. 1.

As depicted in FIG. 3, the protective cap 7 is removed from the syringe assembly 1 prior to injection.

Figure 4:
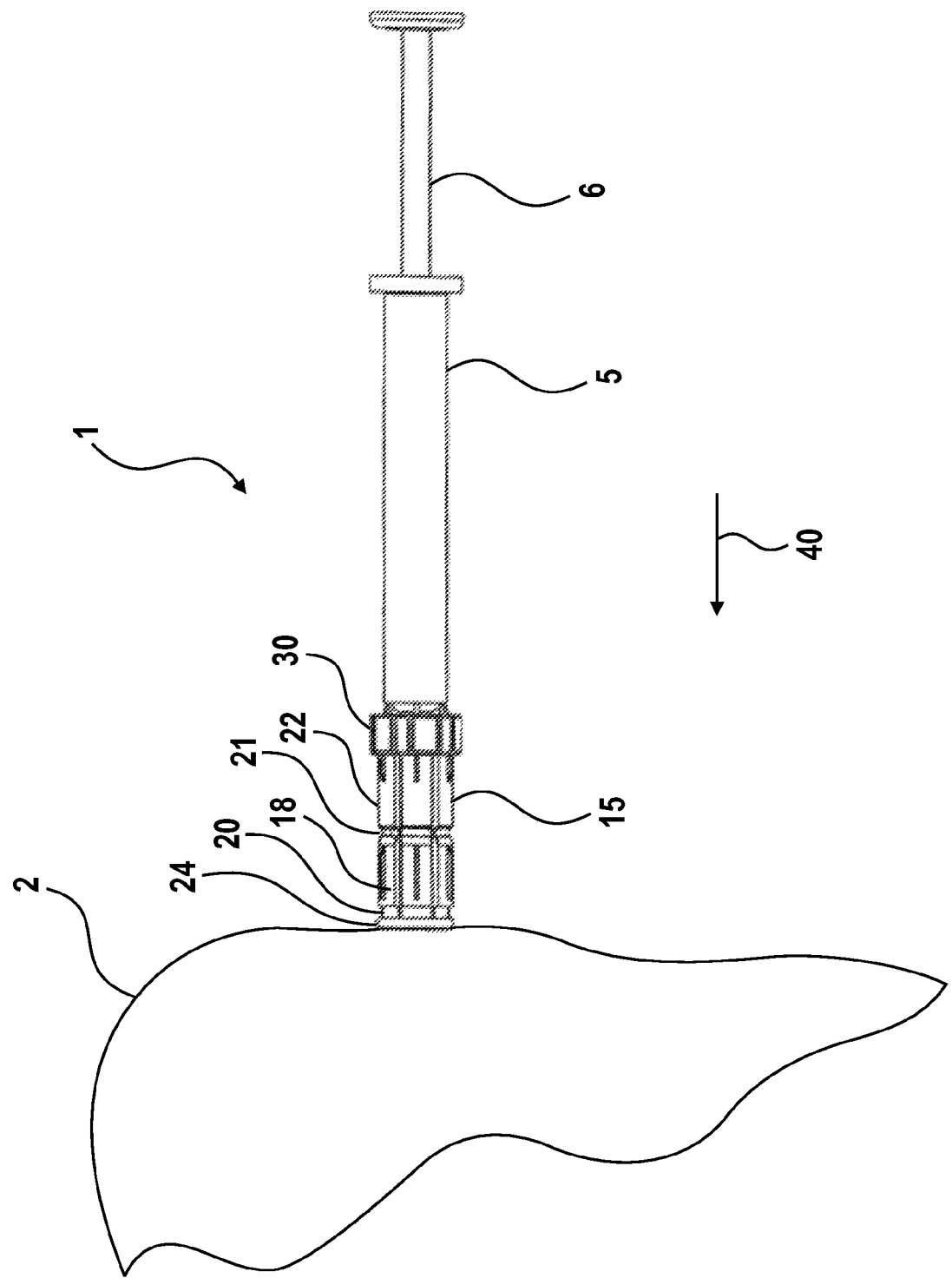
FIG. 4 depicts a side view of the syringe assembly in contact with a patient prior to an injection.

Turning to FIG. 4, to conduct an injection using the syringe assembly 1, the syringe assembly 1 is advanced along injection path 40 to make contact with tissue of a patient 2, placing the collar 24 of the folding panel needle guard 15 into contact with the patient 2.

Figure 5A:
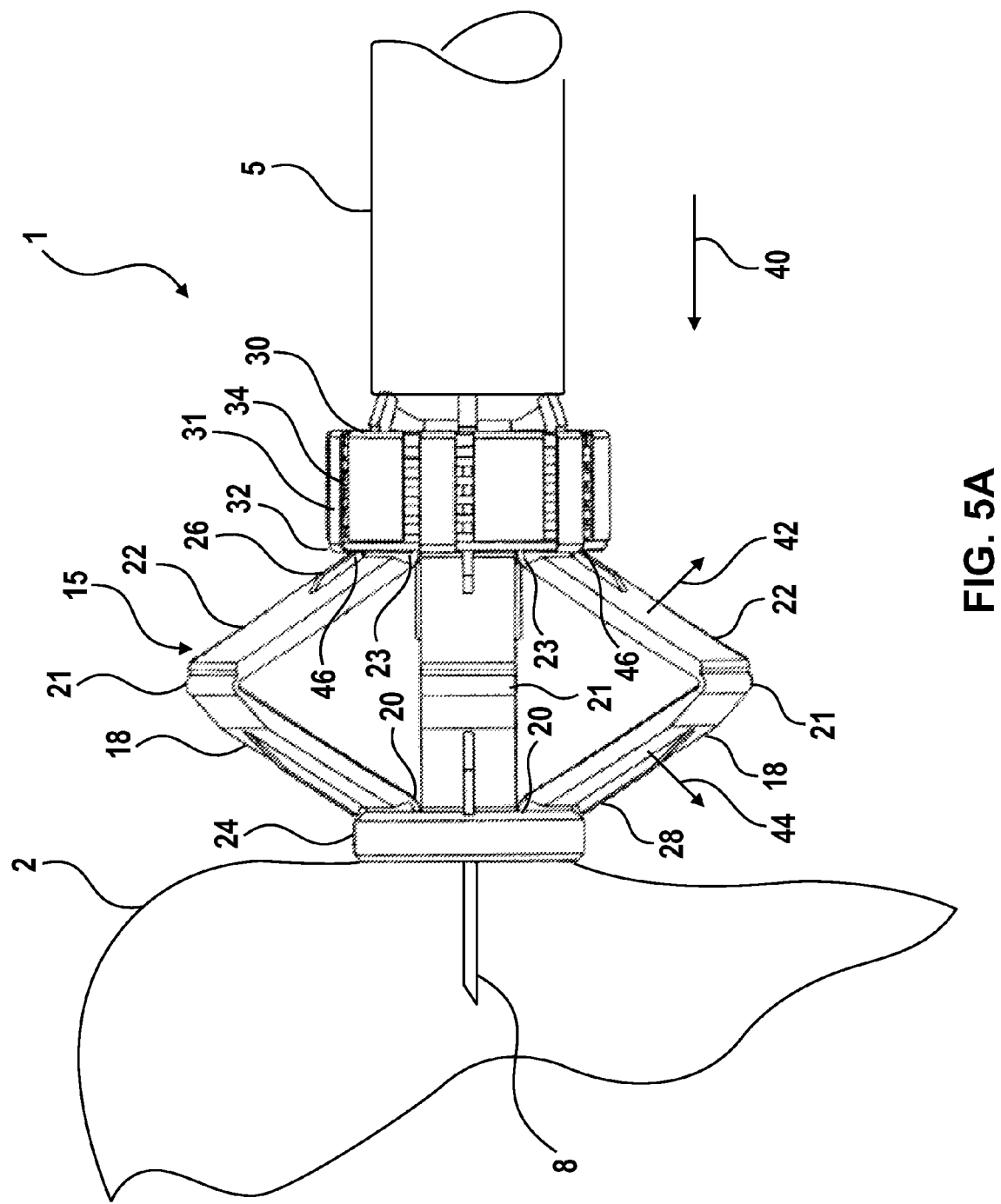
FIG. 5A depicts a side view of the syringe assembly with the needle partially inserted into the patient and the folding panel needle guard partially folded.
Figure 5B:
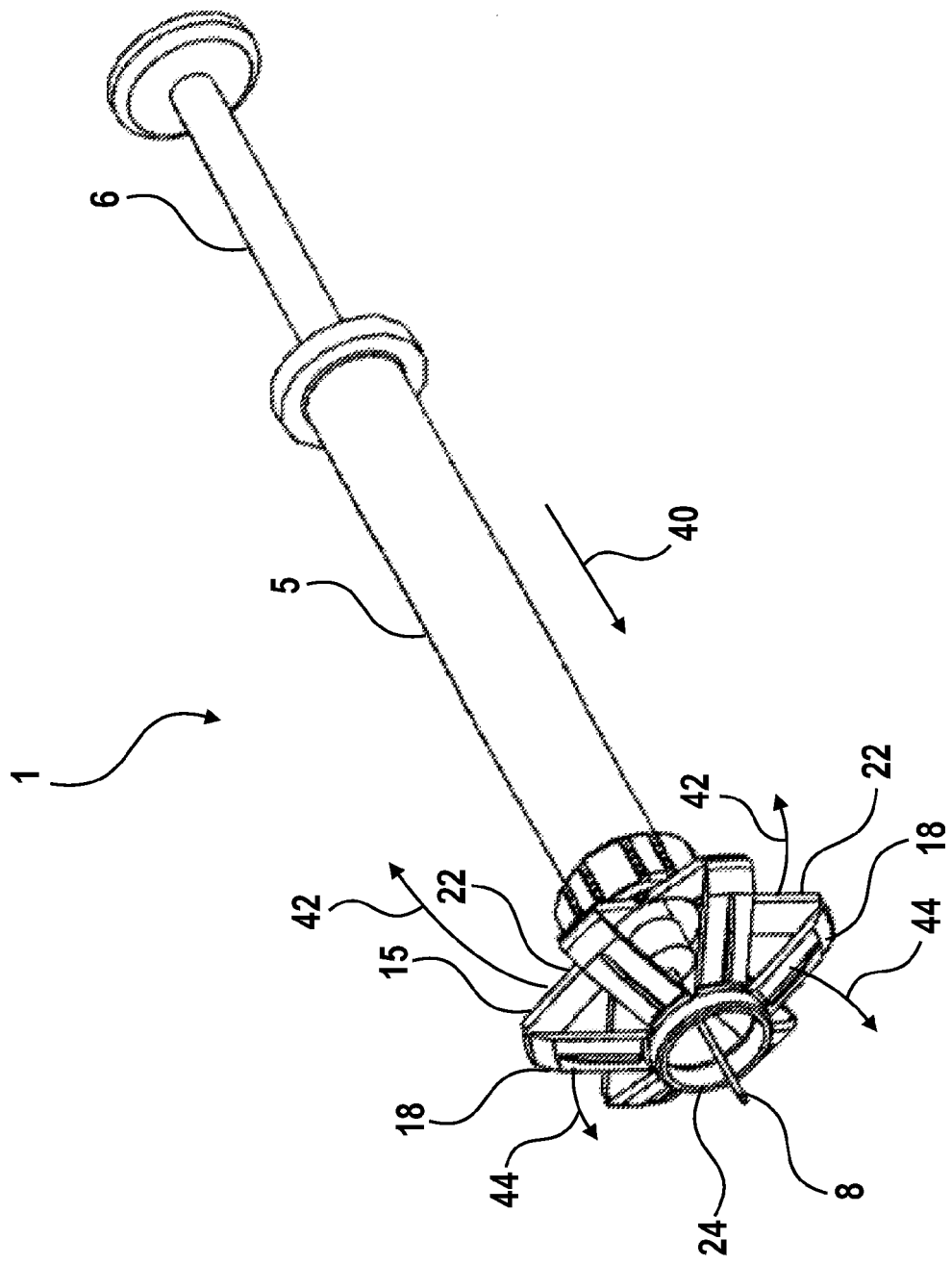
FIG. 5B depicts a perspective view of the syringe assembly with the folding panel needle guard partially folded as shown in FIG. 5A.

As depicted in FIGS. 5A and 5B, the folding panel needle guard 15 collapses towards the base of the needle 8. Referring to FIG. 5A, the syringe assembly 1 is advanced further along injection path 40, collapsing the folding panel needle guard 15 against patient 2. As shown, the collar 24 is in contact with patient 2. The front panels 18 attach to the collar 24 at the hinges 20 and the rear panels 22 at the hinges 21. The rear panels 22 attach to the guard base element 17 (see FIG. 6A) at the hinges 23. The front panels 18 fold at hinges 20 and 21 approximately along a substantially rotational front panel folding path 44. The rear panels 22 fold at hinges 21 and 23 approximately along a substantially rotational rear panel folding path 42. As the folding panel needle guard 15 collapses against the patient 2, the needle 8 is exposed and enters the patient 2.

As shown in FIG. 5A, the folding panel needle guard 15 includes a hub 30 encasing a spring 34. The hub 30 includes latch hooks 32 at end of latch arms 31 spaced about the circumference of the hub 30. The spring 34 is held in compression by the latch hooks 32. As shown in FIGS. 5A and 6C, as the rear panels 22 fold up along the rear panel folding path 42, trigger ribs 26 on the rear panels 22 contact the spring 34 at trigger rib contact points 46, and begins to further compress spring 34.

Figure 6A:
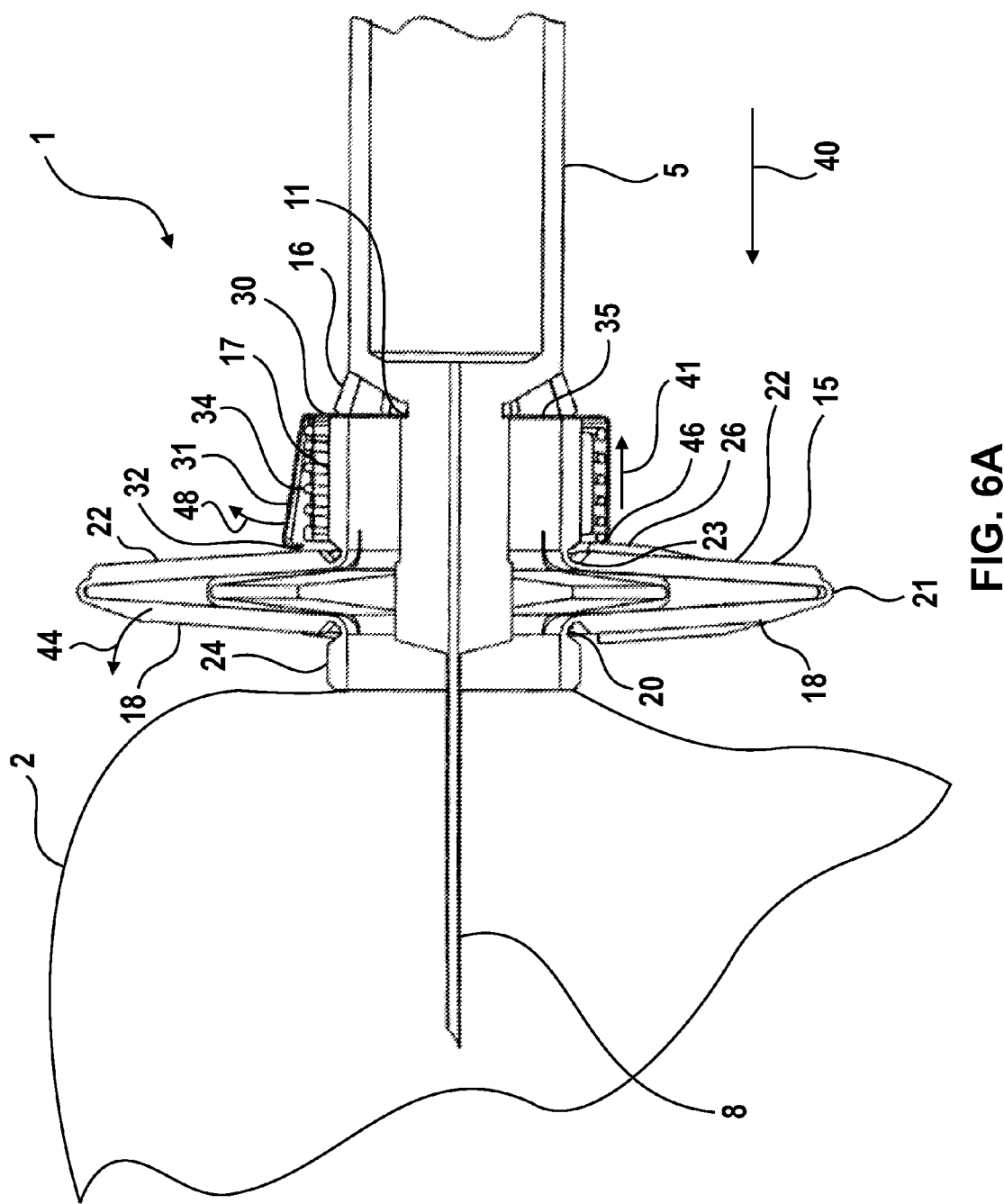
FIG. 6A depicts a side view of the syringe assembly with the needle fully inserted into the patient, the folding panel needle guard fully folded and the spring released.
Figure 6B:
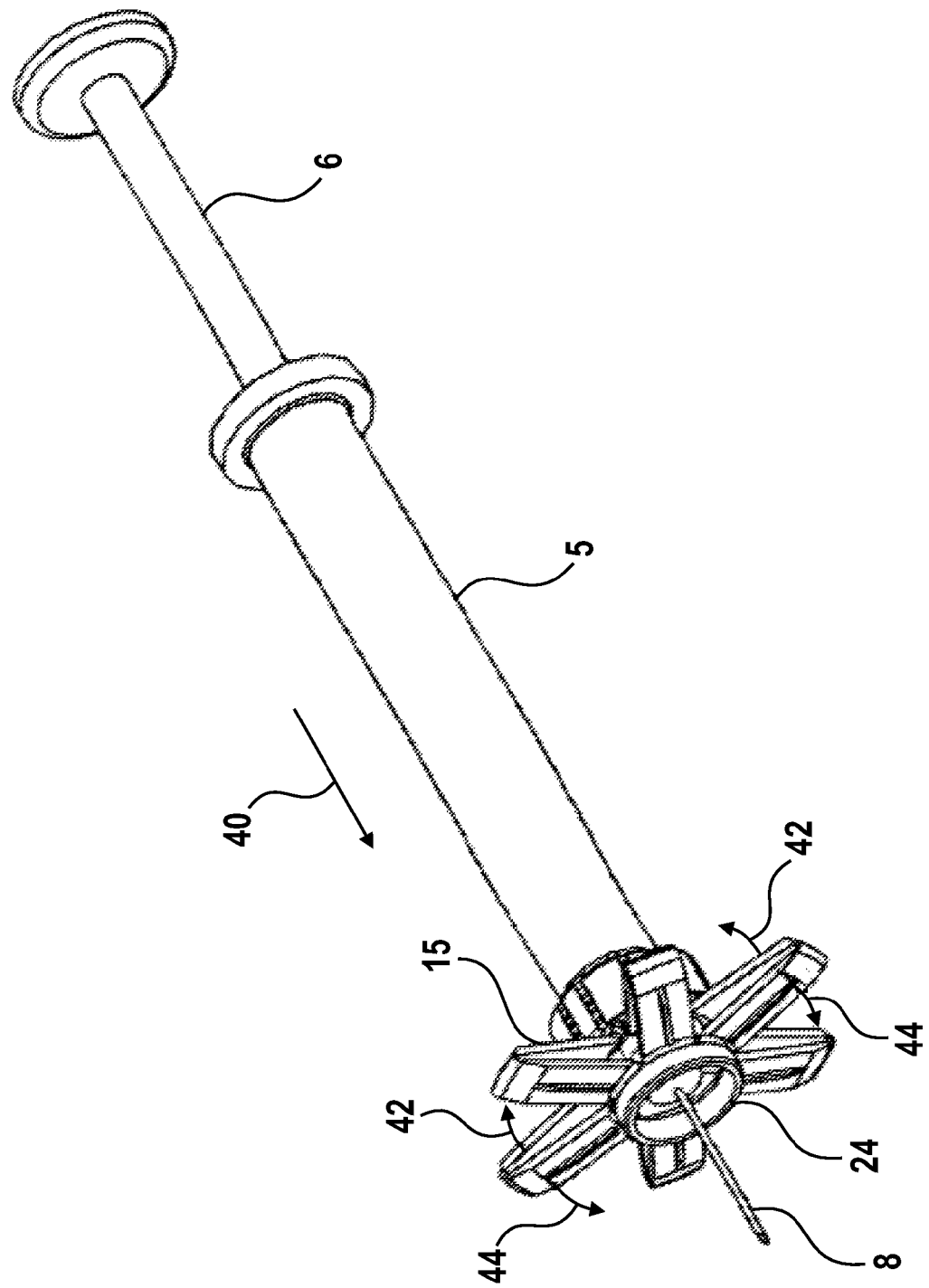
FIG. 6B depicts a perspective view of the syringe assembly with the folding panel needle guard fully folded and the spring released as shown in FIG. 6A.
Figure 6C:
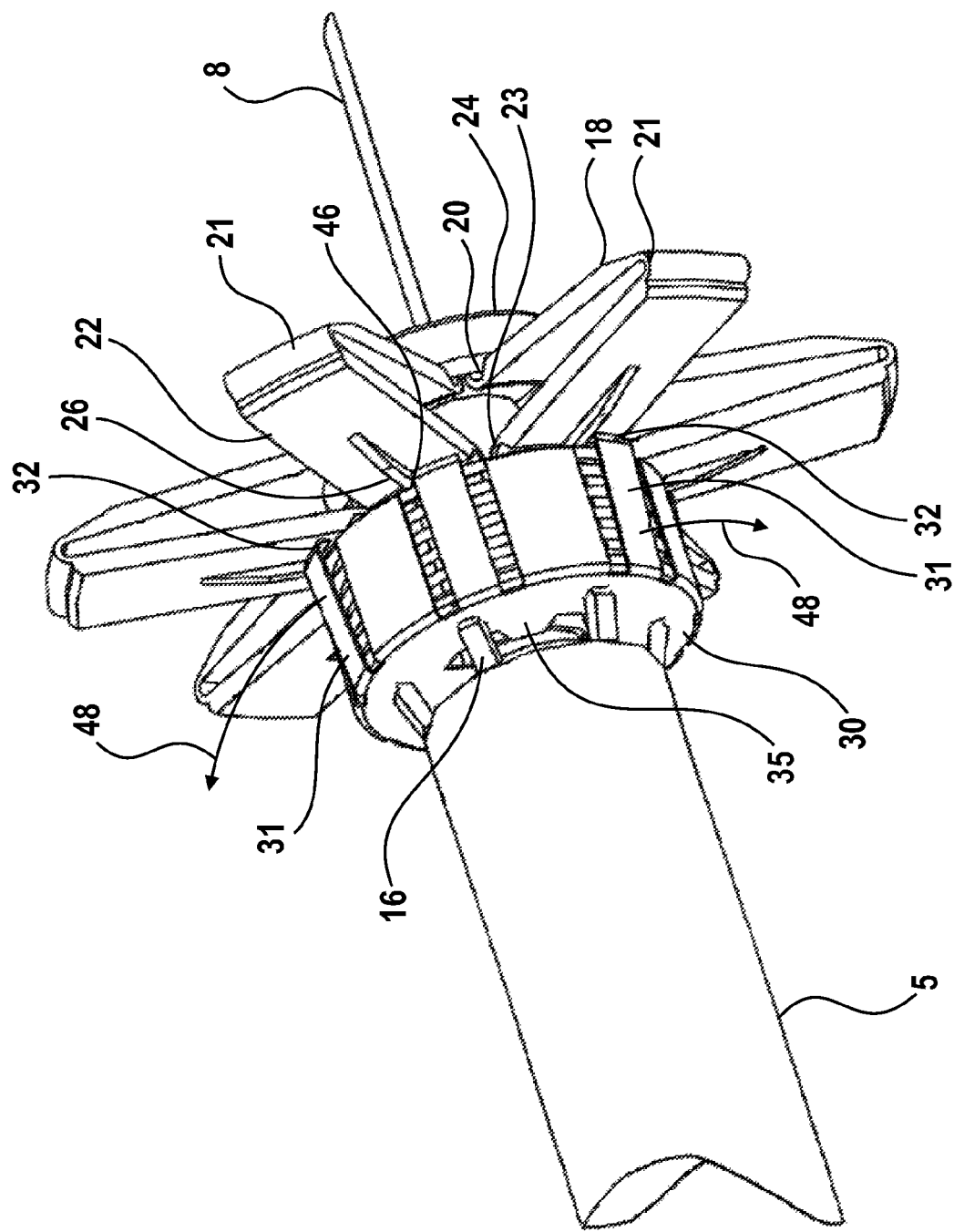
FIG. 6C depicts a partial reverse perspective view of the syringe assembly with the folding panel needle guard fully folded and the spring released as shown in FIG. 6B.

Turning to FIGS. 6A, 6B and 6C, the folding panel needle guard 15 is shown collapsed further with the needle 8 fully exposed. Referring to FIG. 6A, as depicted, the syringe assembly 1 is advanced further along the injection path 40 further collapsing the folding panel needle guard 15 against the patient 2. The needle 8 is further exposed and is deeper into the patient 2. The front panels 18 have folded further at the hinges 20 and 21, and have rotated further along the front panel folding path 44. The rear panels 22 have folded further at the hinges 21 and 23 and have rotated further along the rear panel folding path 42. Referring to FIG. 6C, the trigger ribs 26 have further compressed the spring 34 along spring compression path 41. The latch hooks 32 are now clear from the spring 34, allowing the latch arms 31 to resile, i.e., move outward toward their natural position along trigger arm release path 48, thereby lifting latch hooks 32 out of the path of the spring 34.

As depicted in FIGS. 6A and 6C, an annular end plate 35 of the hub 30 is received in the annular recess 11 formed in the needle hub 3 of the syringe 5. Tabs 16 circumferentially spaced about the plate 35 extend proximally from the plate 35 and abut the distal end of the barrel of the syringe 5 to secure the plate 35 in the annular recess 11.

Figure 7:
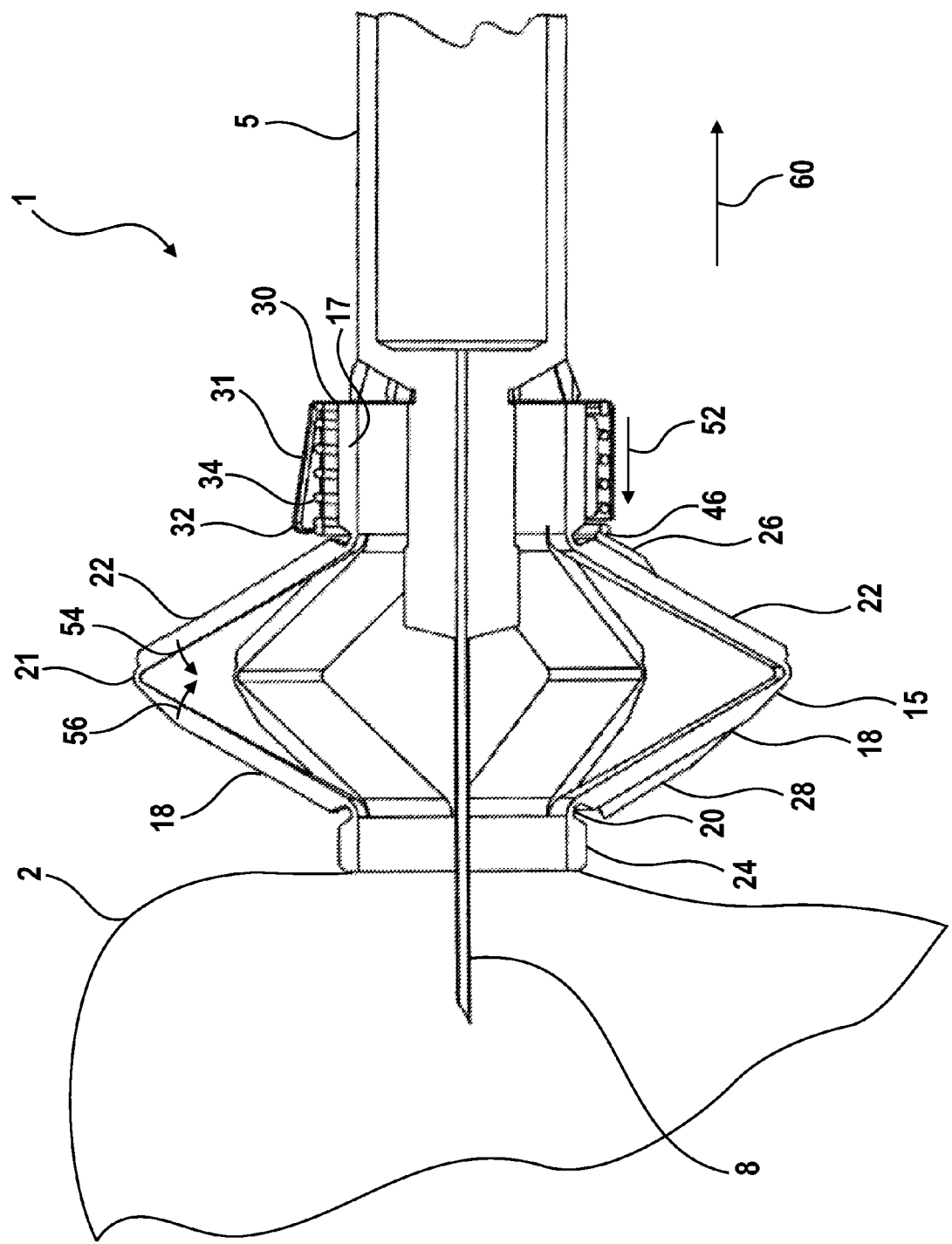
FIG. 7 depicts a side view of the syringe assembly with the needle partially removed from the patient, the folding panel needle guard partially unfolded, and the spring partially extended.

Referring to FIG. 7, the syringe assembly 1 is shown being withdrawn from patient 2 along retraction path 60. With the collar 24 still in contact with the patient 2, the folding panel guard 15 begins to return under the bias of the spring 34 to its original shape as the syringe assembly 1 is withdrawn from the patient 2 along the retraction path 60. As shown, the front panels 18 unfold along the front panel unfolding path 56 and the rear panels 22 unfold along the rear panel unfolding path 54. As depicted, the spring 34 resiles along spring extension path 52, pushing on the rear panels 22 at trigger rib contact points 46 against the trigger ribs 26, and urging the rear panels 22 to unfold, and flatten out, along rear panel unfolding path 54. The front panels 18 (joined to the rear panels 22 at the hinges 21) unfold and flatten out, in response to the motion of the rear panels 22, along the front panel unfolding path 56.

Figure 8A:
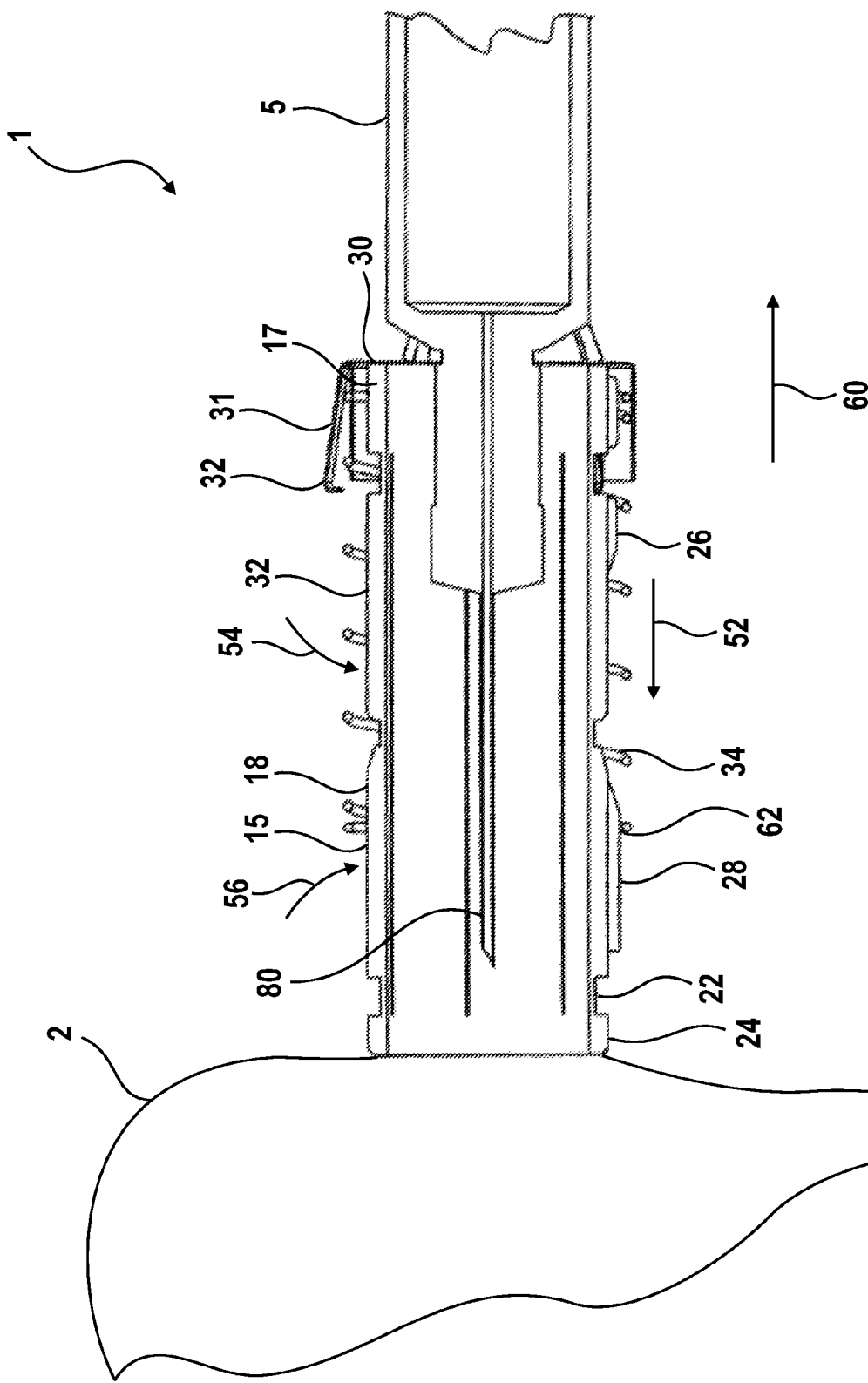
FIG. 8A depicts a side view of the syringe assembly with the folding panel needle guard fully unfolded and the spring fully extended.
Figure 8B:
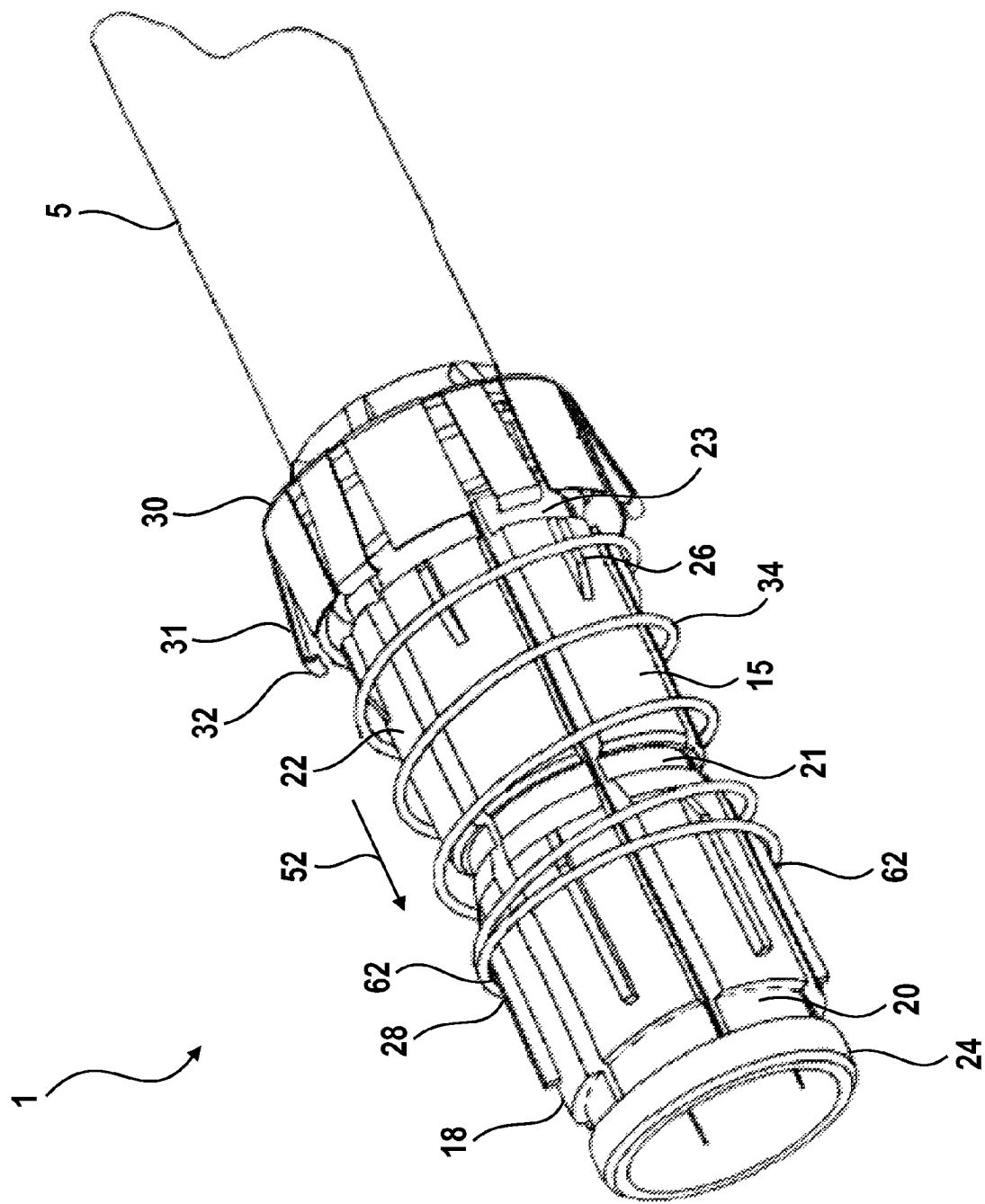
FIG. 8B depicts a partial perspective view the syringe assembly with the folding panel needle guard fully unfolded and the spring fully extended as shown in FIG. 8A.

Turning to FIGS. 8A and 8B, the front panels 18 and rear panels 22 are shown substantially returned to their original co-linear alignment. Referring to FIG. 8A, the syringe assembly 1 is shown following injection and immediately prior to breaking contact with patient 2 with the front panels 18 and rear panels 22 substantially returned to their original co-linear alignment. The spring 34 has resiled further along the spring extension path 52, and is concentric with (and substantially enclosing) the folding panel needle guard 15. The front panels 18 and rear panels 22 are thus substantially locked by the spring 34 in their original co-linear alignment. Optionally, a lock rib 28 may be provided on the front panels 18 to reduce play and provide a spring-rib contact point 62.

Turning now to FIGS. 9A-19 which show another embodiment of a folding panel needle guard 115. As depicted in FIGS. 9A, 9B, 9C and 9D, a syringe assembly 100 comprises a syringe 105, a protective cap 107 positioned over a needle 108, and a folding panel needle guard 115. The syringe 105 includes a plunger 106 with a rubber stopper on its distal end slidably received in the syringe 105 from a proximal end. The needle 108, shown as a staked needle, extends from a needle hub 103 at a distal end of the syringe 105. The folding panel needle guard 115 is shown coupled to the syringe 105 at an annular recess 112 formed in the needle hub 103. As discussed in detail below, the folding panel needle guard 115 comprises front and rear panels 118 and 122 coupled together at hinges 121, a collar 124 attached to the front panels 118 at hinges 120, a base element 125 coupled to the rear panels 122 at hinges 123, a hub 130, a control ring 140 and a spring 138 to unfold and lock the front and rear panels 118 and 122 in a substantially co-linear needle shielded configuration.

Figure 9A:
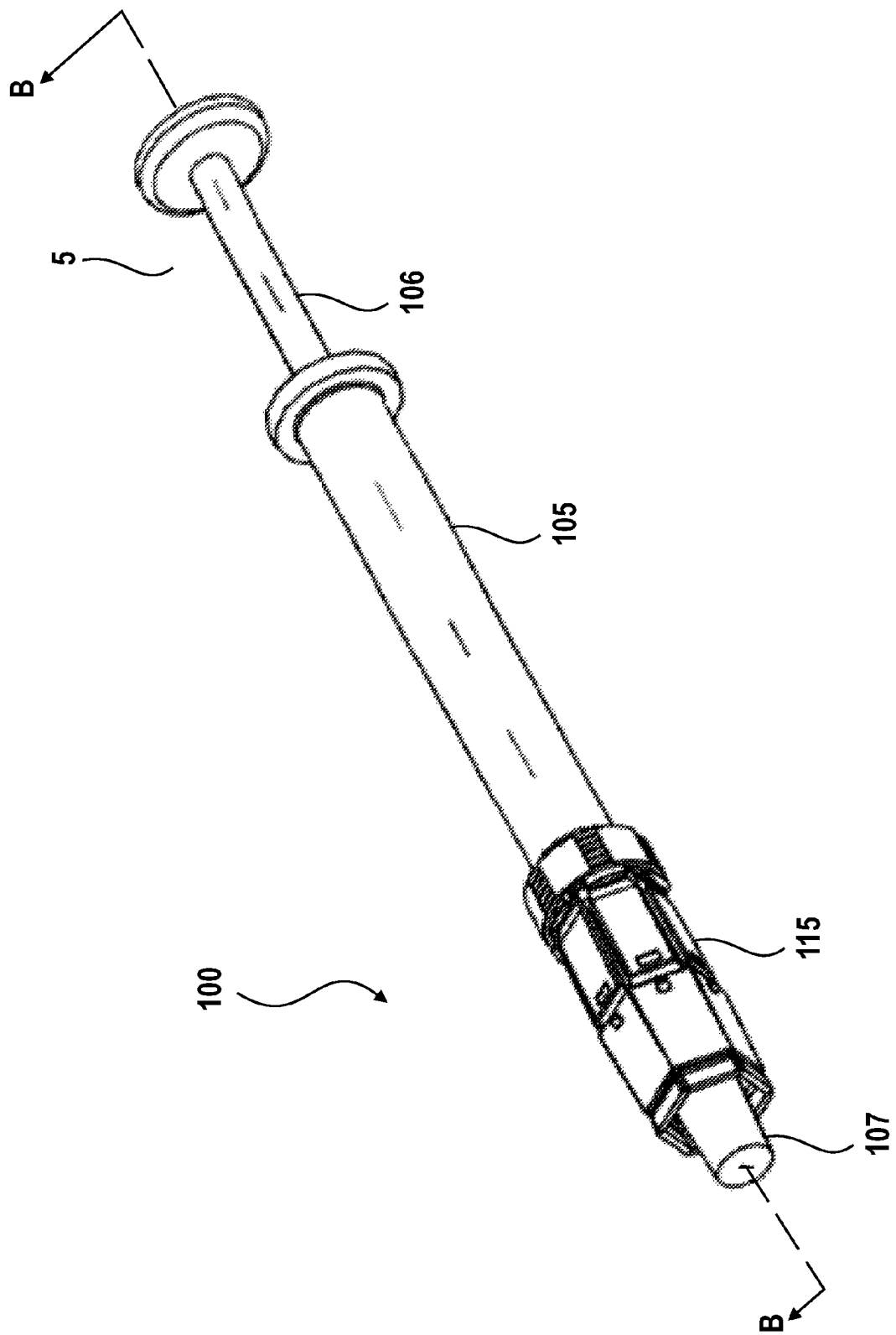
FIG. 9A depicts a perspective view of a syringe assembly comprising a syringe, protective cap, and another embodiment of a folding panel needle guard coupled to the syringe.
Figure 9B:
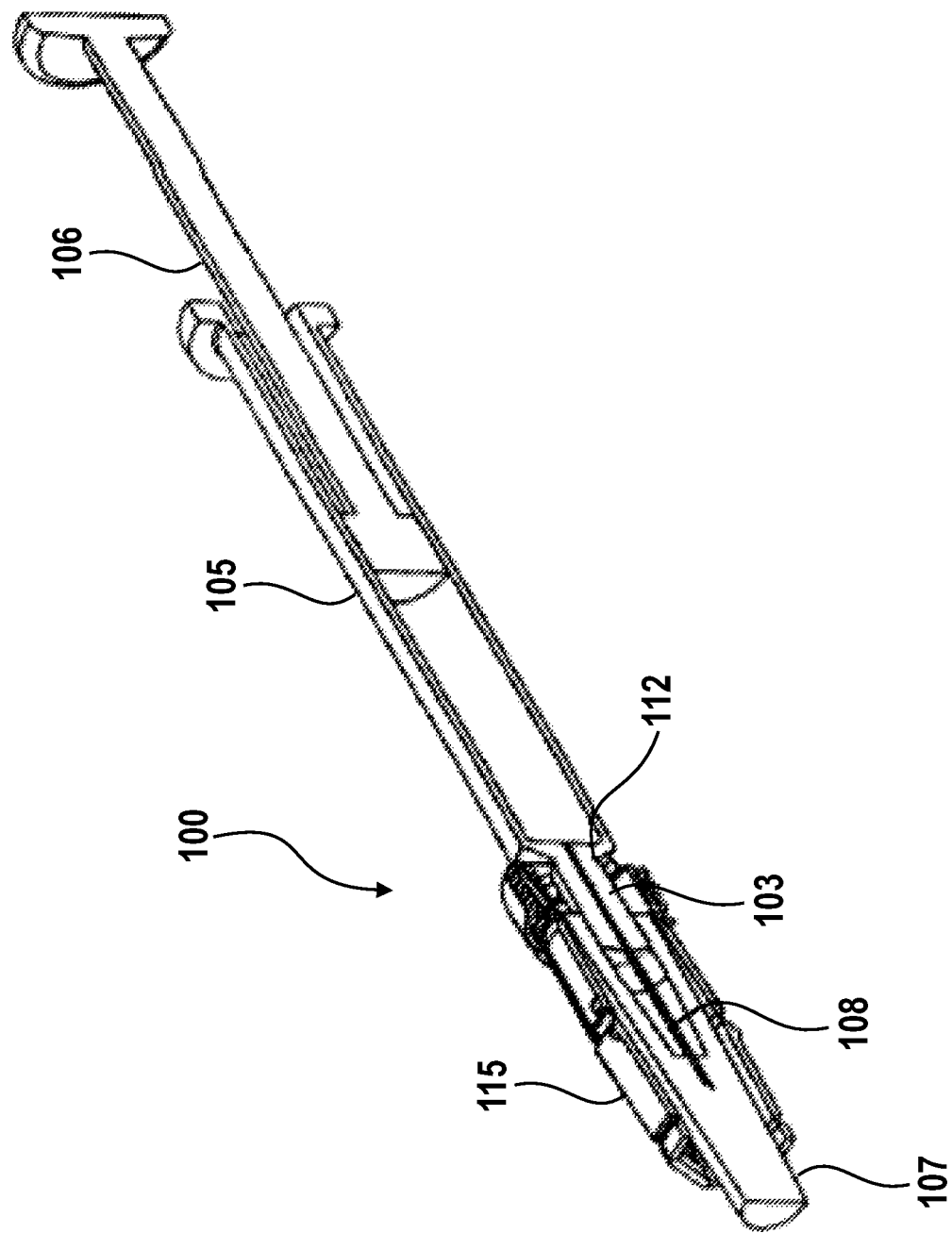
FIG. 9B depicts a sectional perspective view of the syringe assembly taken along line B-B in FIG. 9A.
Figure 9C:
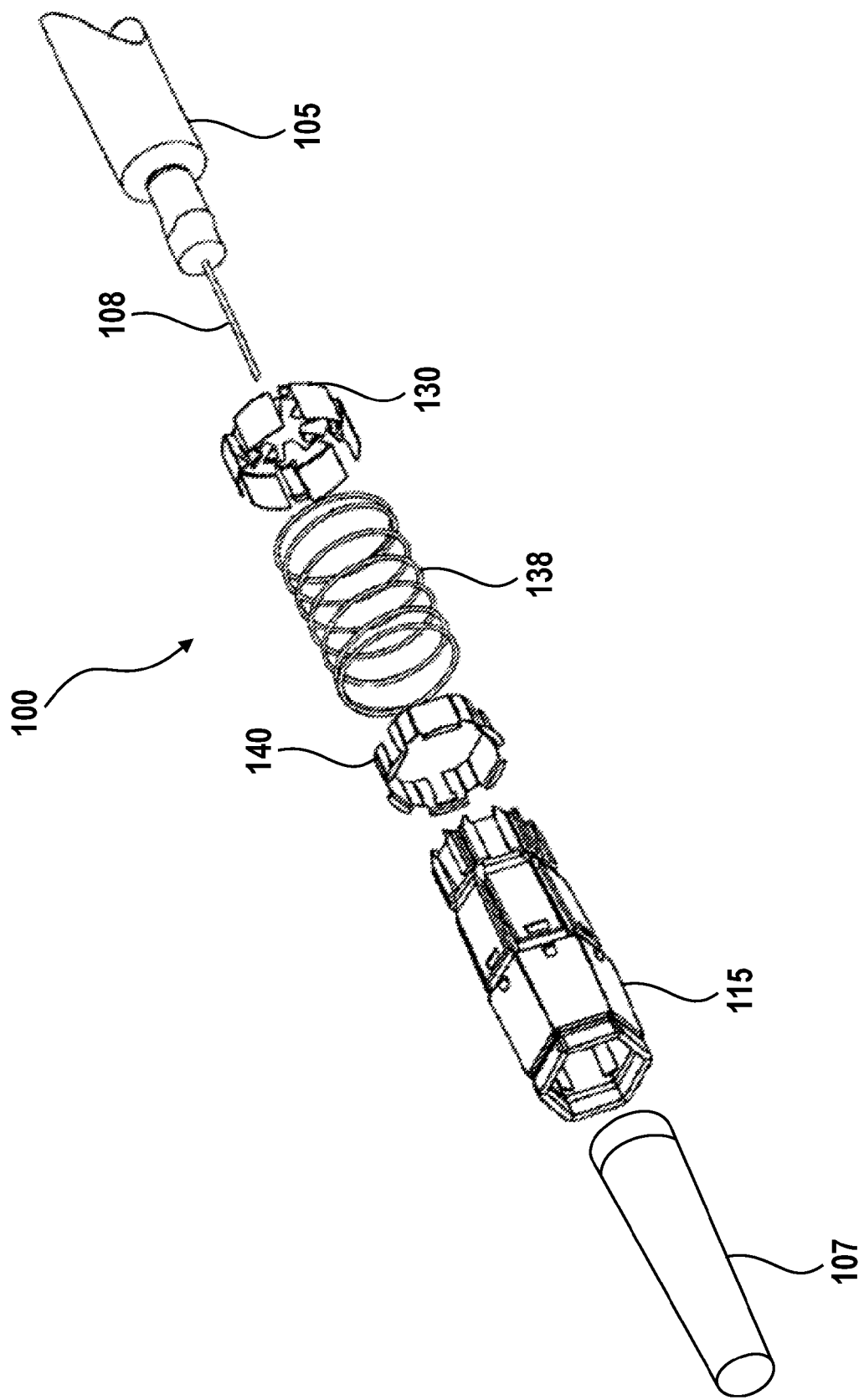
FIG. 9C depicts an exploded partial perspective view of the syringe assembly in FIG. 9A.
Figure 9D:
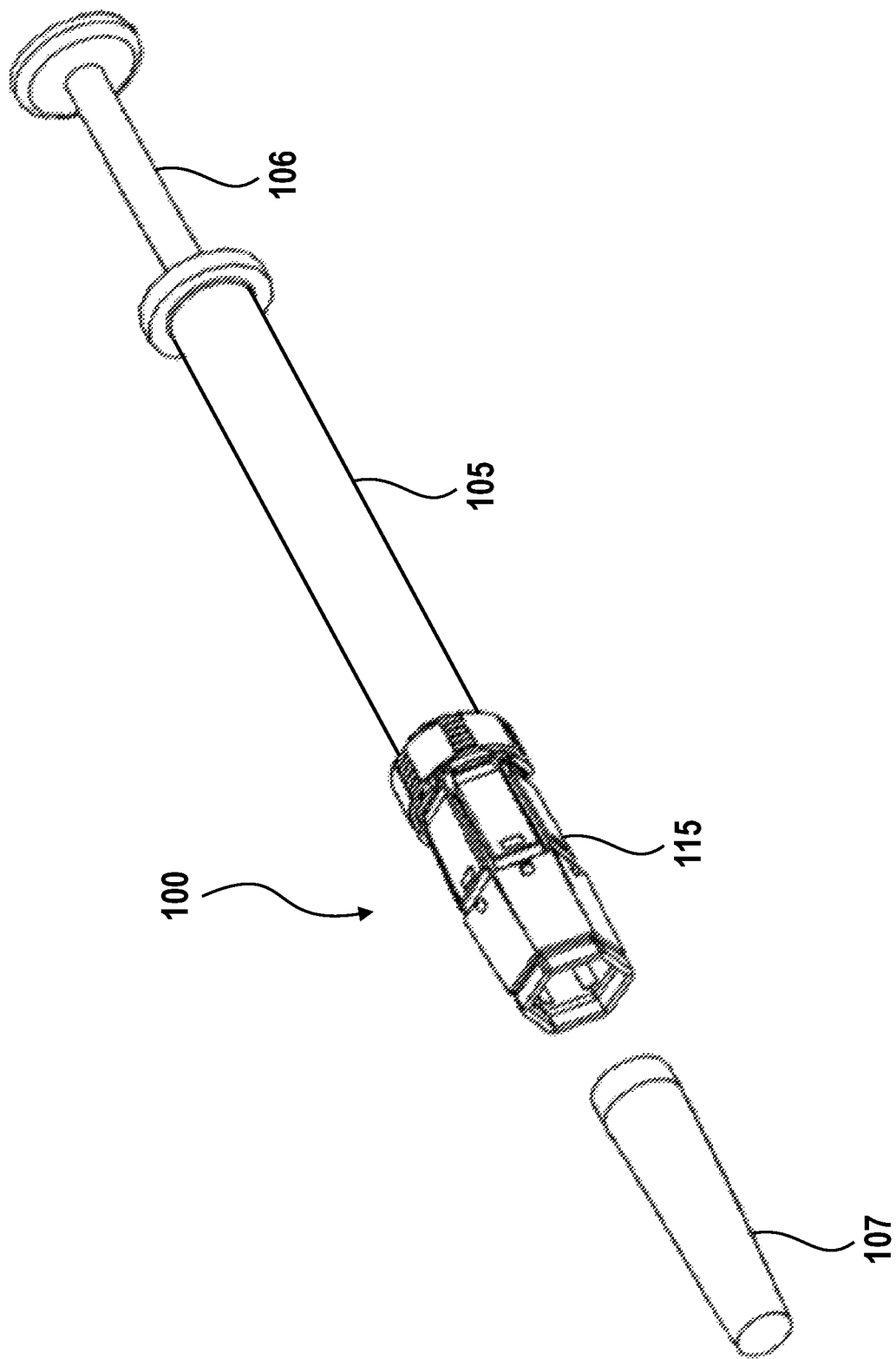
FIG. 9D depicts an partially exploded perspective view of the syringe assembly in FIG. 9A.

As depicted in FIG. 9D, the protective cap 107 is removed from the syringe assembly 100 prior to injection.

Figure 10:
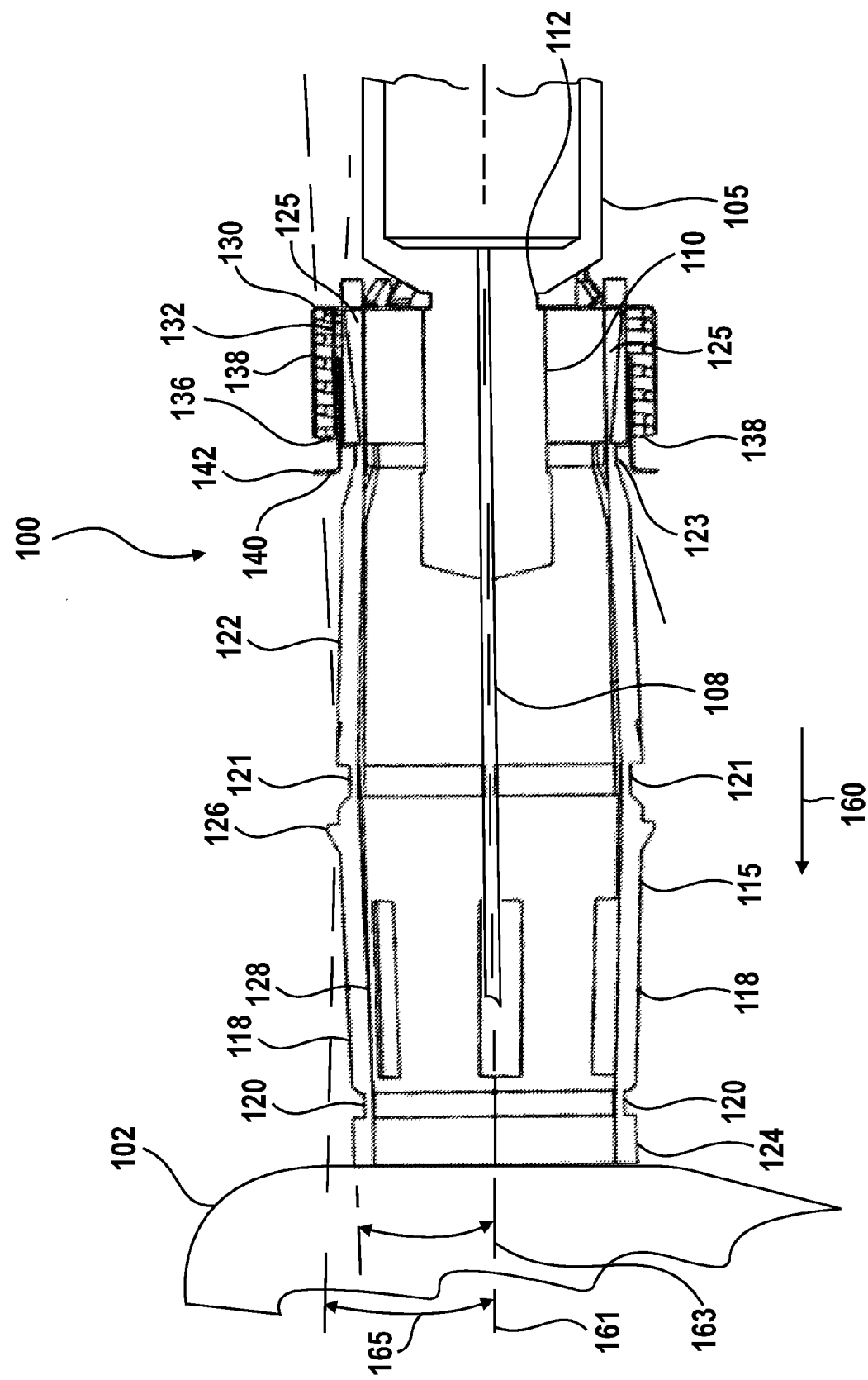
FIG. 10 depicts a partial side view of the syringe assembly in contact with a patient prior to an injection.

Turning to FIG. 10, to conduct an injection using the syringe assembly 100, the syringe assembly 100 is advanced along injection path 160 to make contact with tissue of a patient 102, placing the collar 124 of the folding panel needle guard 115 into contact with the patient 102. The folding panel guard 115 is shown just prior to initiation of collapse of the panels with the collar 124 in contact with the patient 102. The front panels 118 connect to the collar 124 at the hinges 120 and to the rear panels 122 at the hinge 121. The front panels 118 may be biased relative to a central axis 161 by a front panel bias angle 163. The rear panels 122 connect to the front panel 118 at the hinges 121 and to the base element 125 at the hinges 123. The rear panel 122 may be biased relative to the central axis 161 by a rear panel bias angle 165. The bias angles 163 and 165 in the folding panel needle guard 115 may be provided by molding, coining or other modification steps, or by other means. The hinges 120, 121 and 123 may be living hinges, pivoting hinges, hooks, links, or other known hinge elements. The hinges 120, 121 and 123 may be formed into the folding panel needle guard 115 during manufacture (e.g. during injection molding), or may be added to the folding panel needle guard 115 during manufacture (e.g. by addition of another component or material).

Figure 11A:
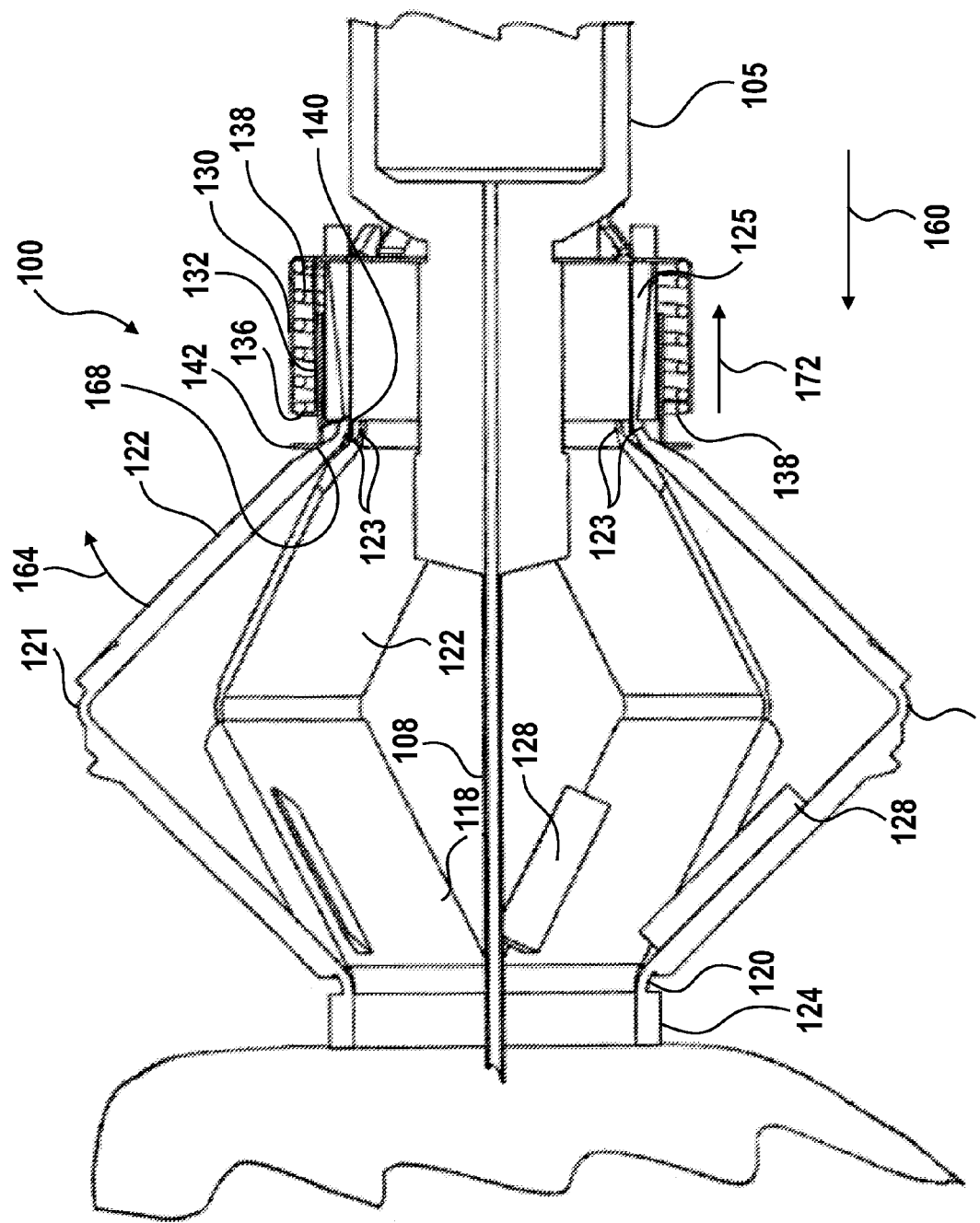
FIG. 11A depicts a partial side view of the syringe assembly with the needle partially inserted into the patient and the folding panel needle guard partially folded.

As depicted in FIG. 11A, the syringe assembly 100 is shown advanced further along injection path 160, with the collar 124 in contact with patient 102 and the folding panel needle guard 115 collapsing against the patient 102, exposing the needle 108. As the syringe assembly 100 advances, the front panels 118 fold at the hinges 120 and 121 approximately along a substantially rotational front panel folding path 166. The rear panels 122 fold at hinges 121 and 123 approximately along a substantially rotational rear panel folding path 164. The needle 108 is exposed and enters the patient 102.

The hub 130 encases the spring 138. The hub 130 includes a latch hook 136 at an end of a latch arm 132. The spring 138 is held in compression by the latch hook 136. As the rear panels 122 fold up along the rear panel folding path 164, the rear panels 122 contact catch hooks 142 of the control ring 140 at control ring contact points 168, and begin to drive the control ring 140 back along a control ring trigger path 172. The motion of the control ring 140 along the control ring trigger path 172 will, as explained below, eventually result in the release of the spring 138.

Figure 11B:
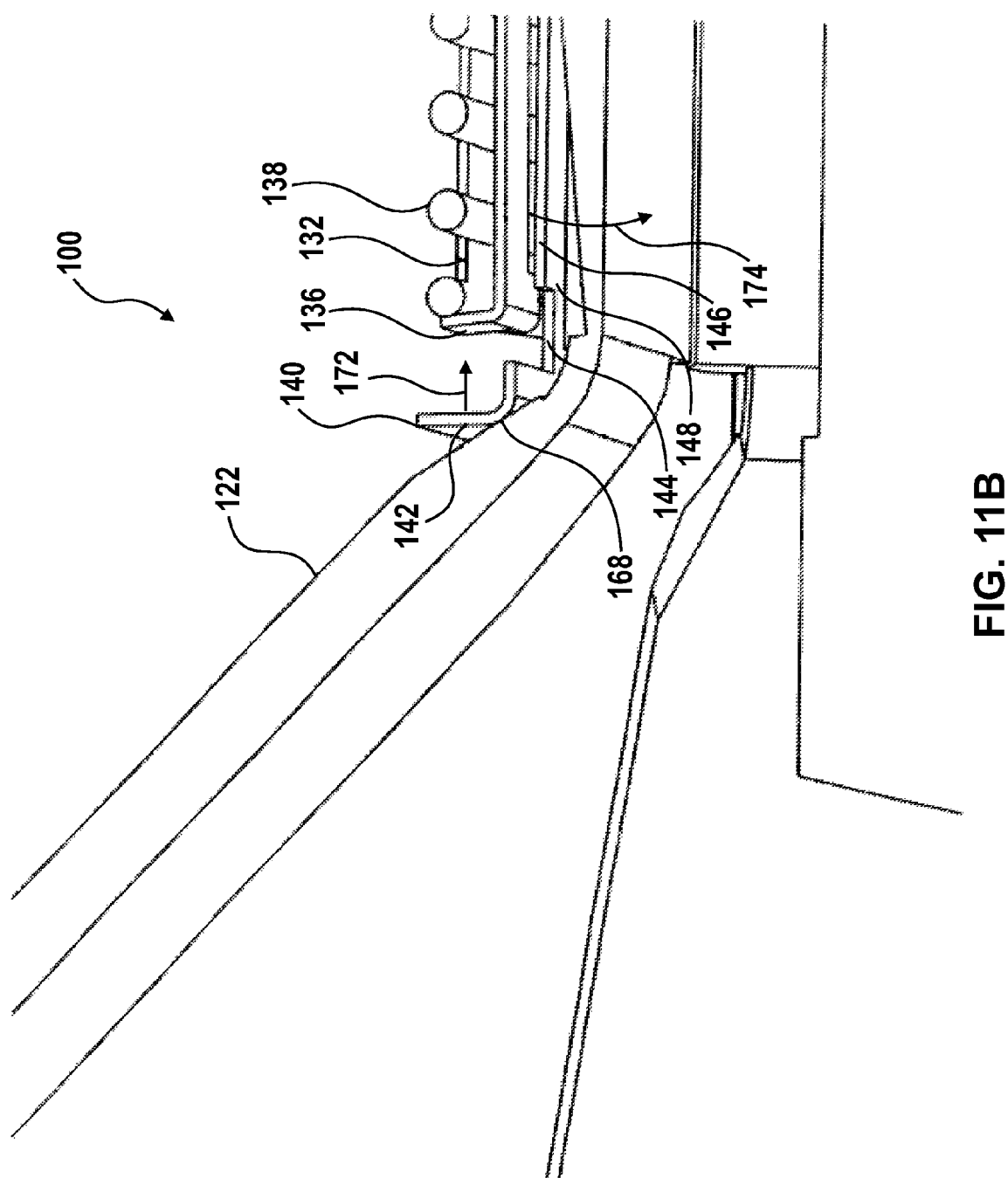

Referring to FIG. 11B, a detail view from FIG. 11A, shown partially from the underneath, of the relative positions of the control ring 140 and the latch arm 132. The rear panels 122 are shown in contact with the control ring 140 at control ring contact points 168, and driving the control ring 140 back along a control ring trigger path 172. The spring 138 is restrained by the latch hooks 136 at an end of the latch arms 132. The latch arms 132 are biased to deflect downward along a latch arm release path 174, but are prevented from doing so by interference between a latch arm tab 148 and a control ring tab 146.

Figure 12A:
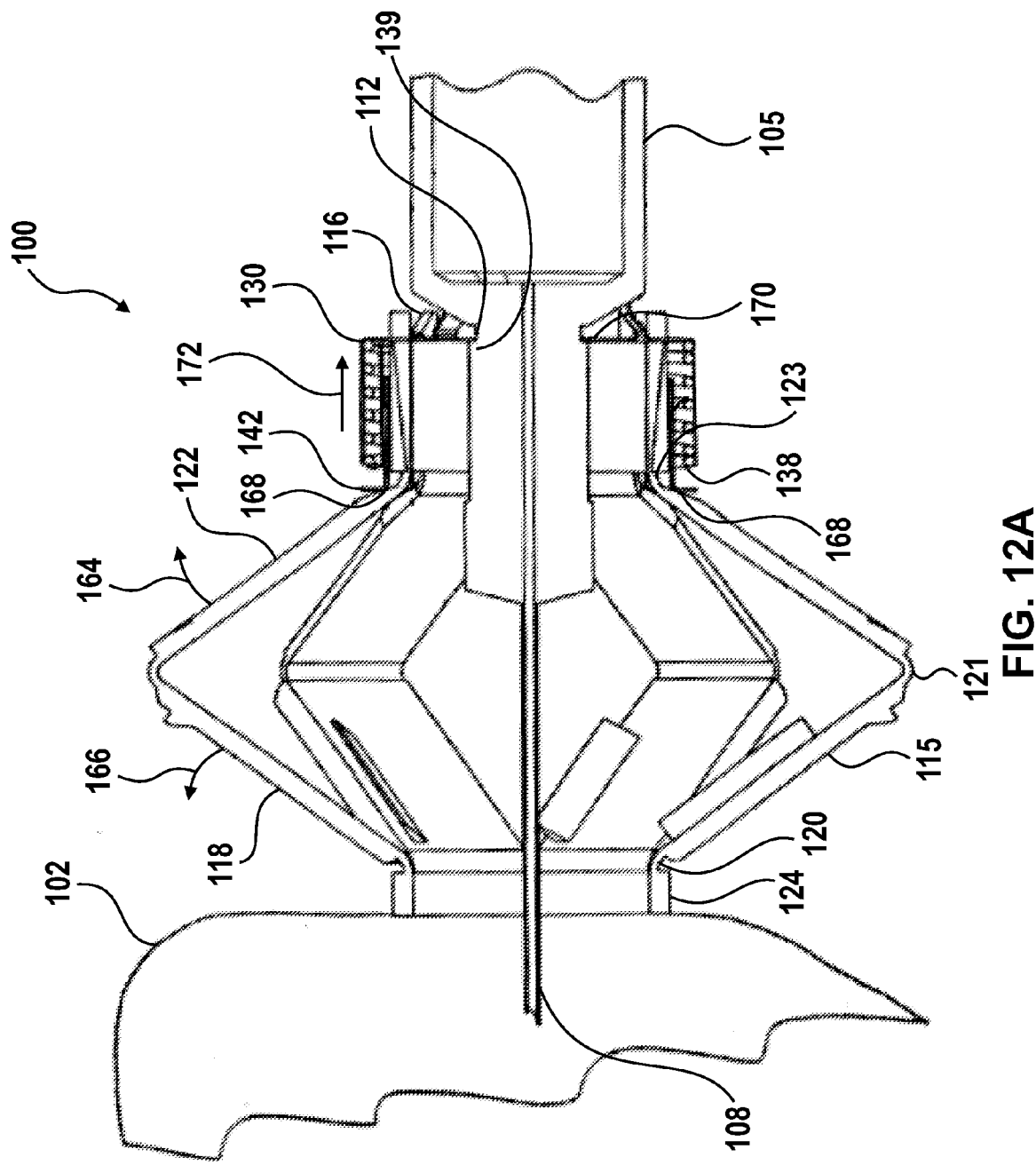
FIG. 12A depicts a partial side view of the syringe assembly with the needle partially inserted further into the patient and the folding panel needle guard partially folded further.
Figure 12B:
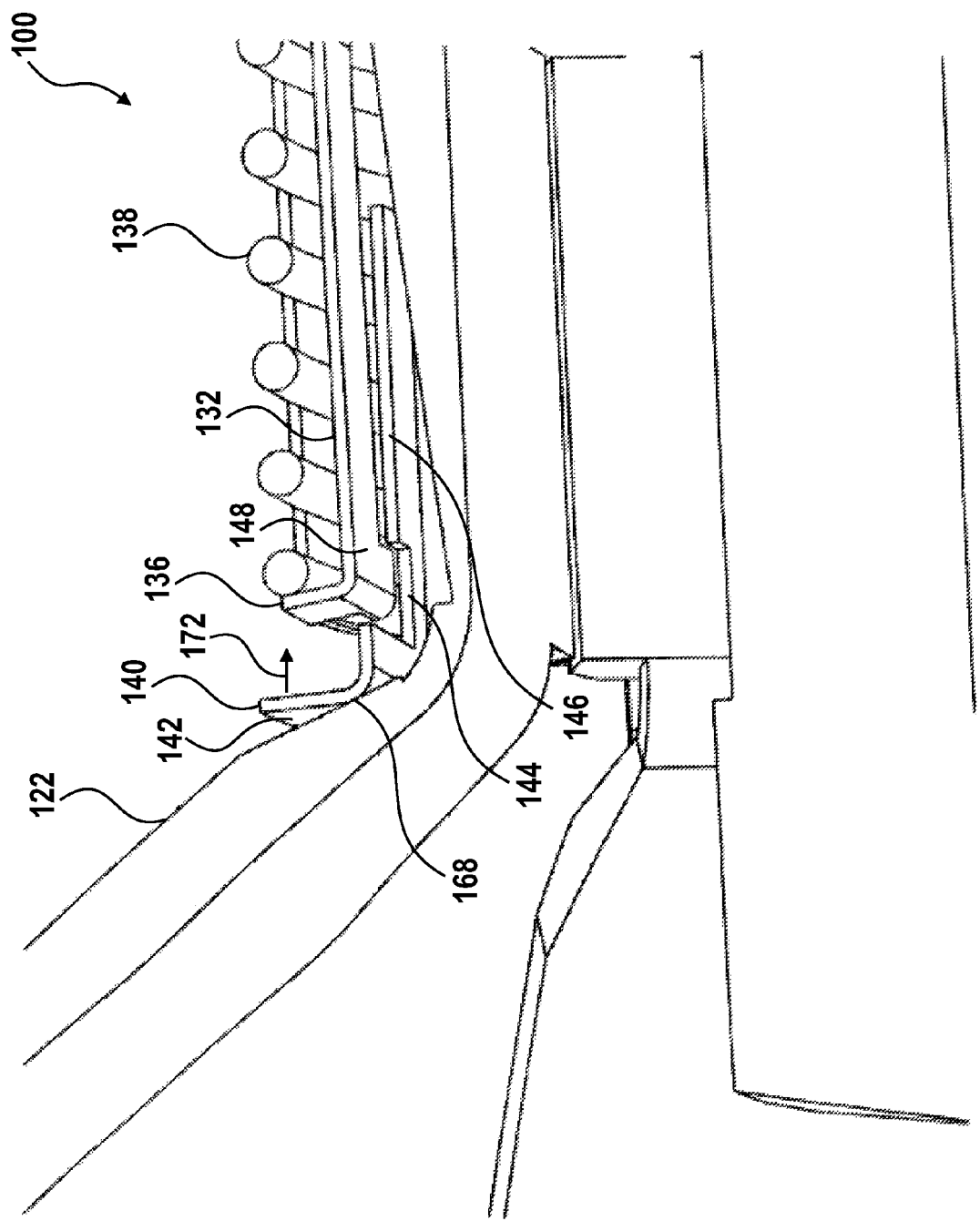
FIG. 12B depicts a detail view from FIG. 12A shown partially from underneath showing the relative positions of the control ring and latch arm as interference is eliminated.

FIG. 12A shows the syringe assembly 100 advanced further along the injection path 160. The needle 108 is shown further exposed and entering the patient 102. As folding panel needle guard 115 collapses, the front panels 118 have folded further along front panel folding path 166, and the rear panels 122 have folded further along rear panel folding path 164. The rear panels 122, which are in contact with control ring 140 at control ring contact points 168, have driven the control ring 140 back further along the control ring trigger path 172. As shown in FIG. 12B, the interference between the latch arm tabs 148 and the control ring tabs 146 is eliminated, and the latch arm tabs 148 are aligned with control ring apertures 144.

Figure 13A:
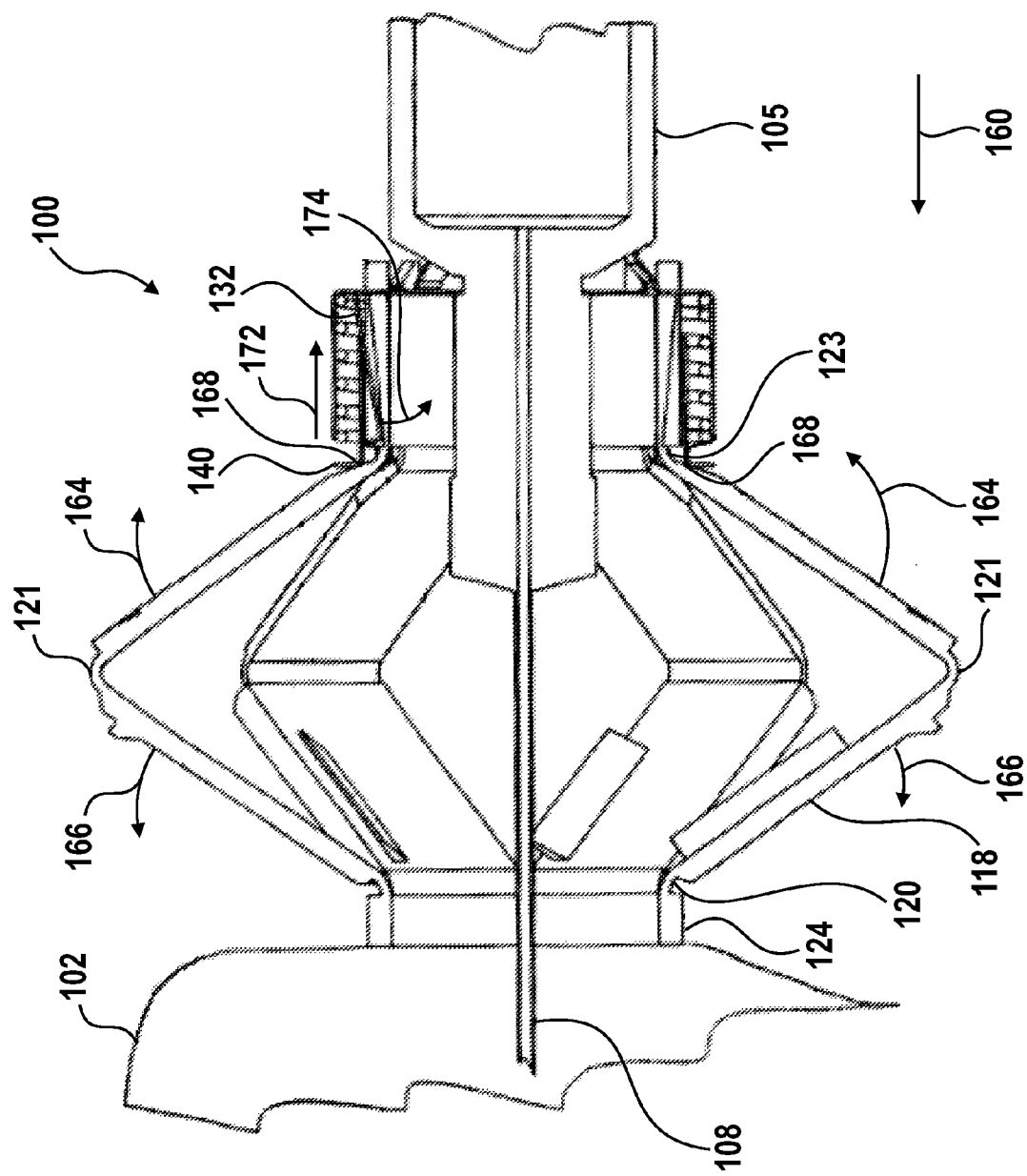
FIG. 13A depicts a partial side view of the syringe assembly with the needle partially inserted further into the patient and the folding panel needle guard partially folded further as the latch arm resiles along release path.
Figure 13B:
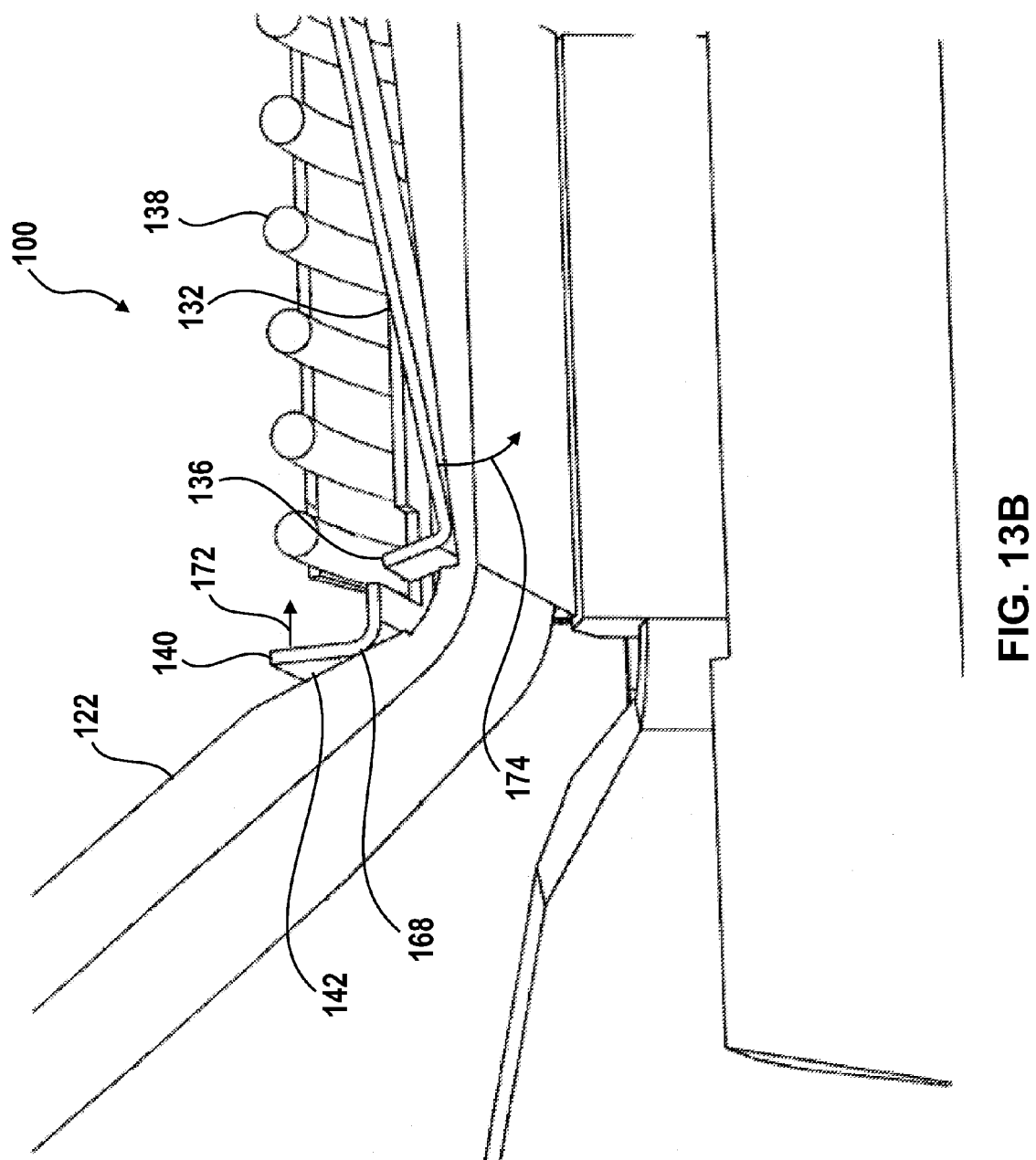
FIG. 13B depicts a detail view from FIG. 13A shown partially from underneath showing the relative positions of the control ring and latch arm as the latch arm resiles along release path and releases the spring.

As shown in FIGS. 13A and 13B, the latch arms 132 resile, i.e., release to their natural biased position along latch arm release path 174, dropping the latch hooks 136 out of the path of the spring 138.

Figure 14A:
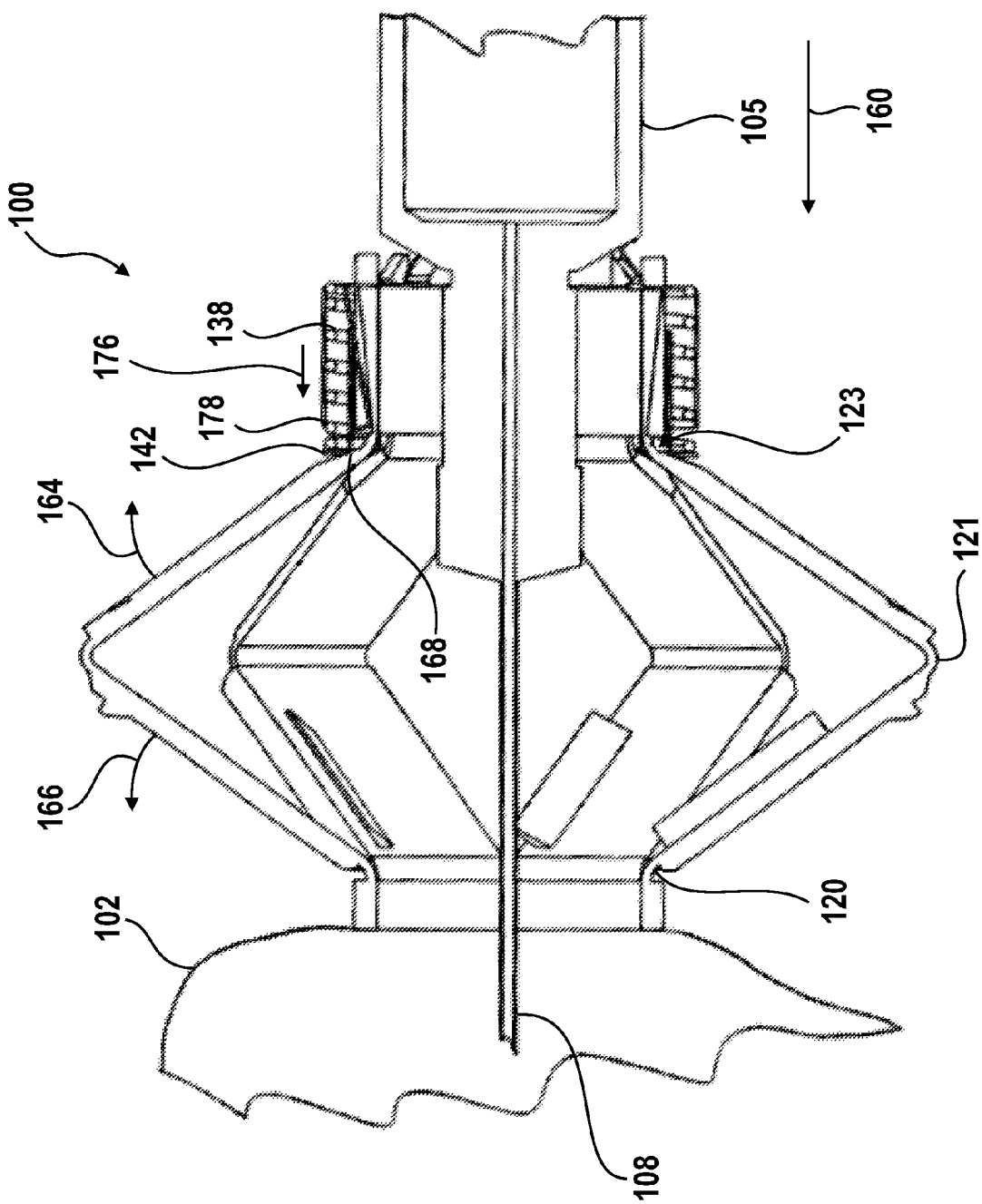
FIG. 14A depicts a partial side view of the syringe assembly as shown in FIG. 13A as the spring resiles along the spring extension patent to make contact with the control ring.
Figure 14B:
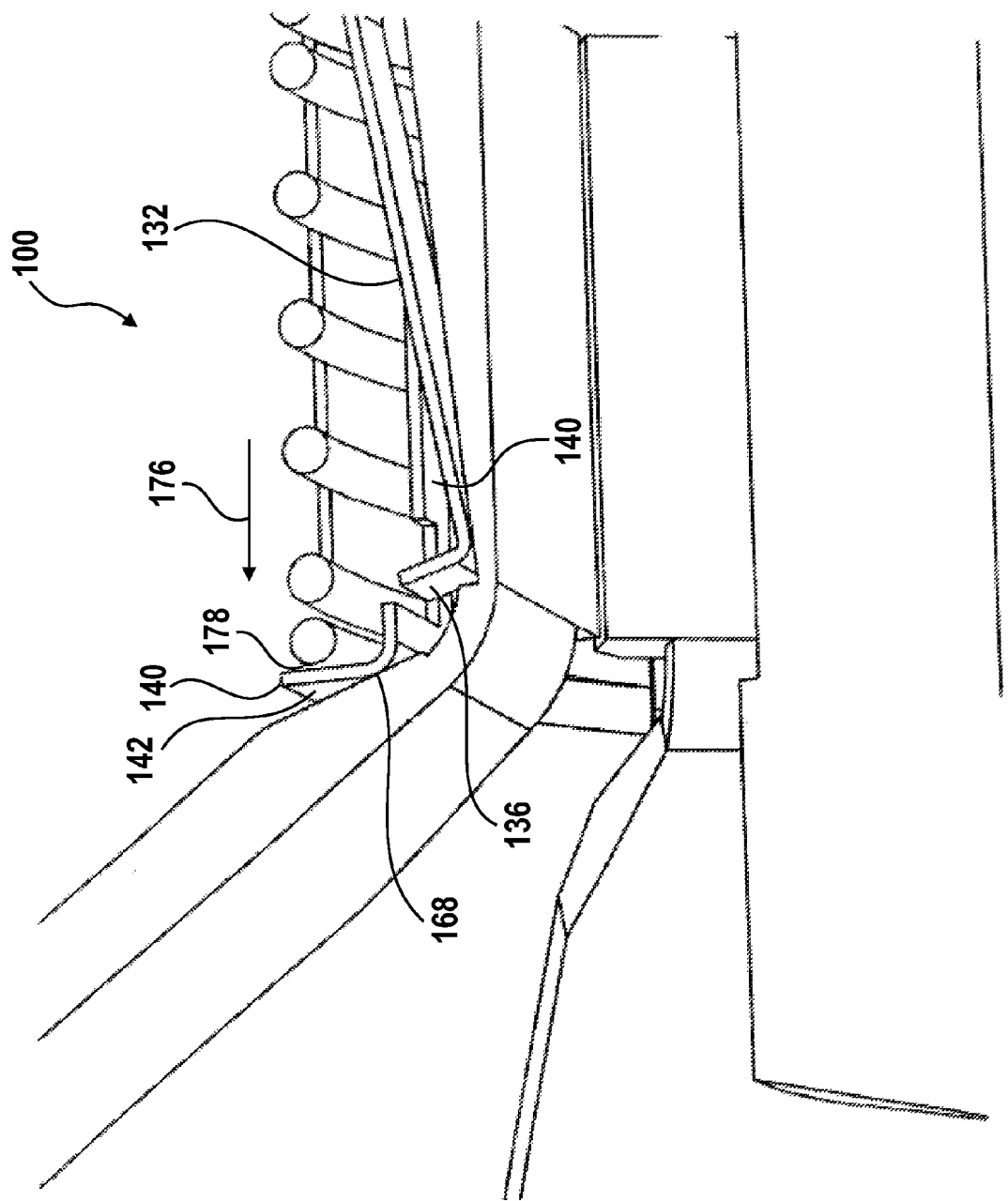
FIG. 14B depicts a detail view from FIG. 14A shown partially from underneath showing the relative positions of the control ring and latch arm as the spring resiles along spring extension path.

As shown in FIGS. 14A and 14B, the spring 138, unrestrained by latch hooks 136, resiles along the spring extension path 176 to make contact with the control ring 140 at control ring pressure points 178.

Figure 15:
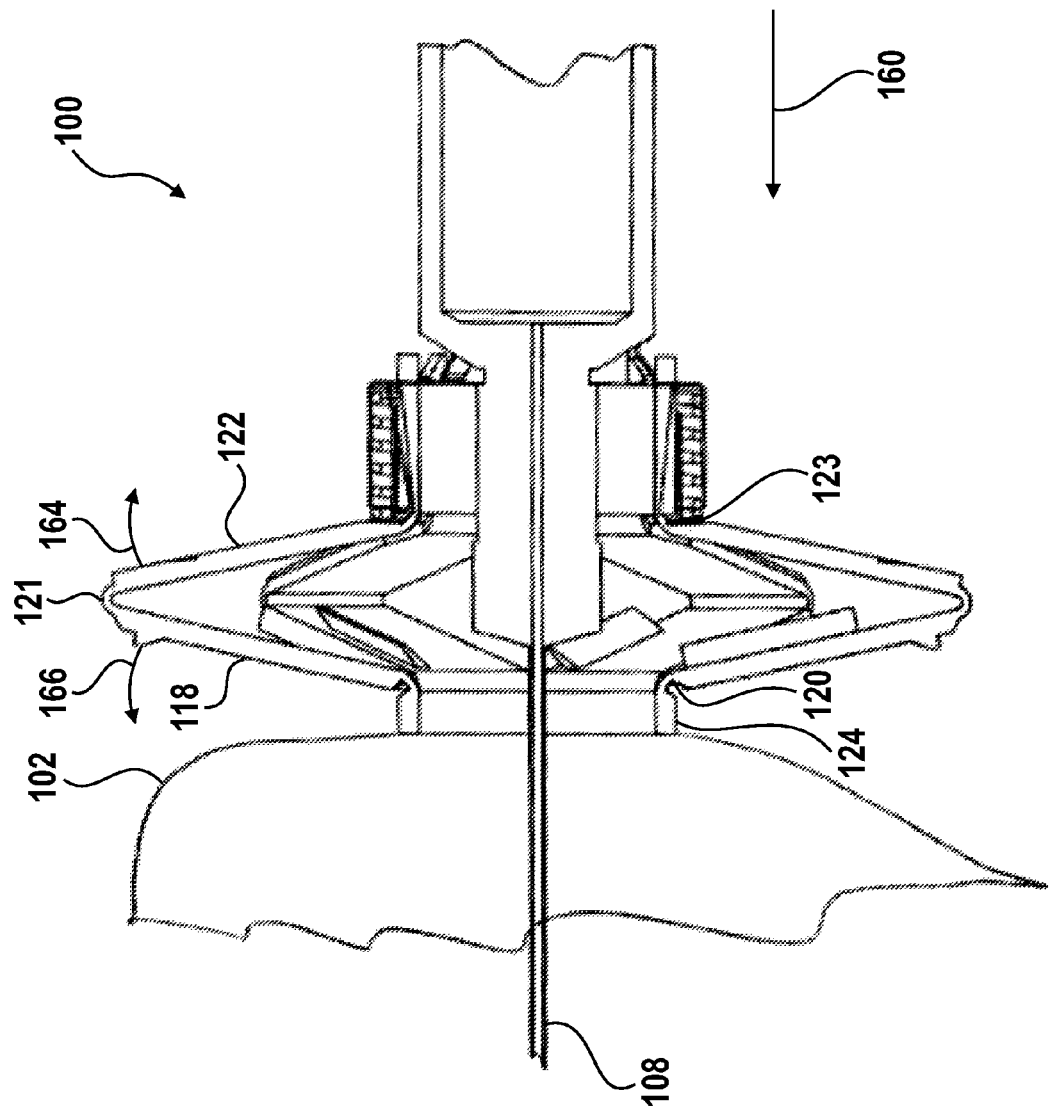
FIG. 15 depicts a side view of the syringe assembly with the needle advanced further into the patient to complete the injection with the panels folded further along the panel folding path.

Turning to FIG. 15, the syringe assembly 100 is shown as it is advanced further along the injection path 160 to complete the injection. As shown, the front panels 118 have folded further along the front panel folding path 166, and the rear panels 122 have folded further along the rear panel folding path 164.

Figure 16:
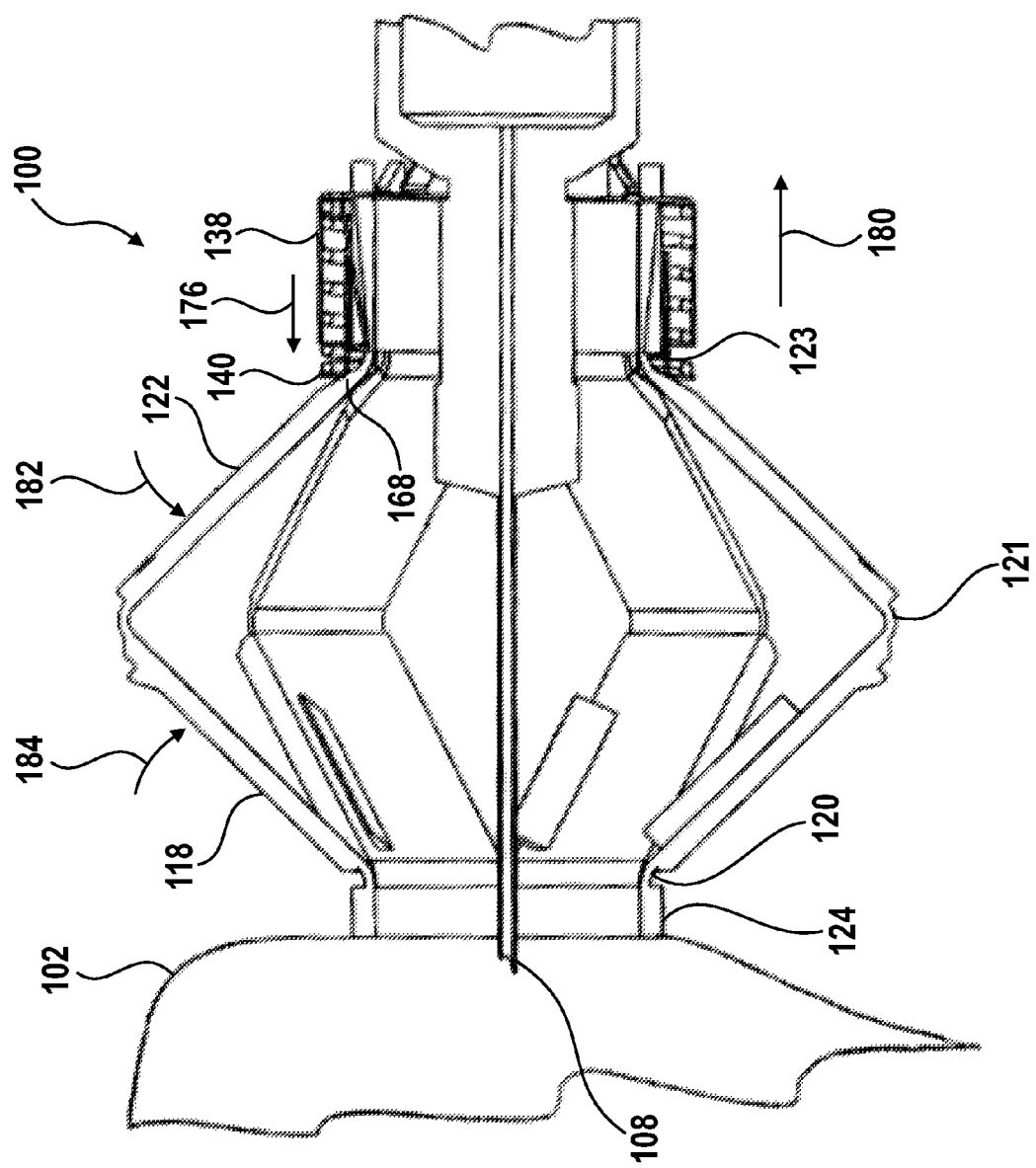
FIG. 16 depicts a side view of the syringe assembly with the needle partially removed from the patient, the folding panel needle guard partially unfolded, and the spring partially extended.

As shown in FIG. 16, the syringe assembly 100 can be withdrawn from the patient 102 along a retraction path 180 after the injection is complete. As the syringe assembly 100 is withdrawn, the front panels 118 unfold along a front panel unfolding path 184 and the rear panels 122 unfold along a rear panel unfolding path 182. The spring 138 resiles along the spring extension path 176, pushing on the control ring 140, which in turn pushes on the rear panels 122 at the control ring contact points 168, thereby urging the rear panels 122 to unfold, and flatten out, along the rear panel unfolding path 182. The front panels 118 (joined to the rear panels 122 at hinges 121) unfold and begin to flatten out, in response to the motion of rear panels 122, along the front panel unfolding path 184.

Figure 17:
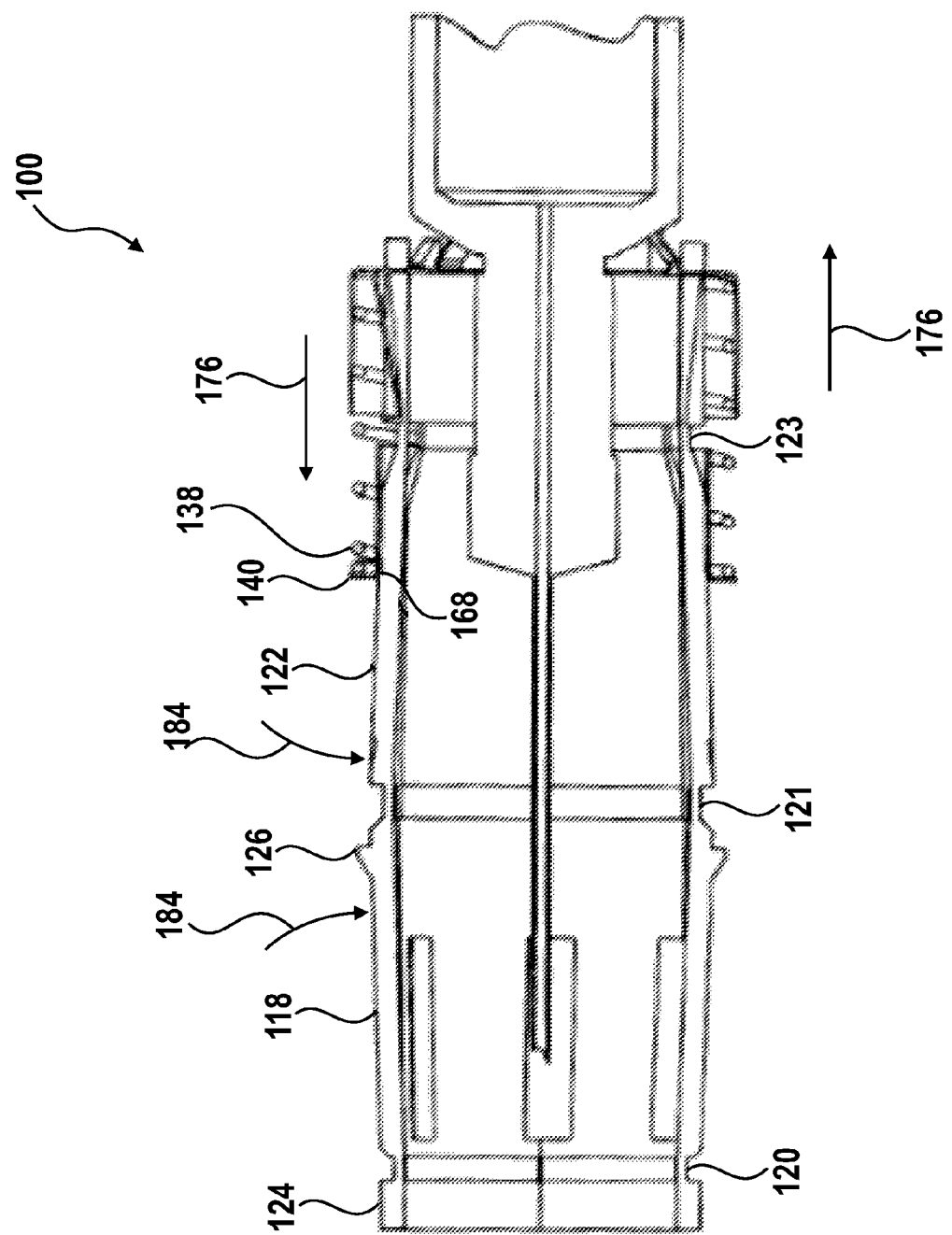
FIG. 17 depicts a side view of the syringe assembly with the folding panel needle guard fully unfolded and the spring partially extended.

Turning to FIG. 17, the syringe assembly 100 is shown withdrawn from the patient 102 along the retraction path 180. As the syringe assembly is withdrawn, the spring 138 continues to resile along the spring extension path 176, pushing on the control ring 140, which in turn pushes on the rear panels 122 at the control ring contact points 168, urging the rear panels 122 to unfold, and flatten out, along the rear panel unfolding path 182. The front panels 118 (joined to the rear panels 122 at hinges 121) unfold and continue to flatten out in response to the motion of the rear panels 122, along the front panel unfolding path 184. Both the front panels 118 and the rear panels 122 have returned to their original, essentially co-linear, alignment.

Figure 18:
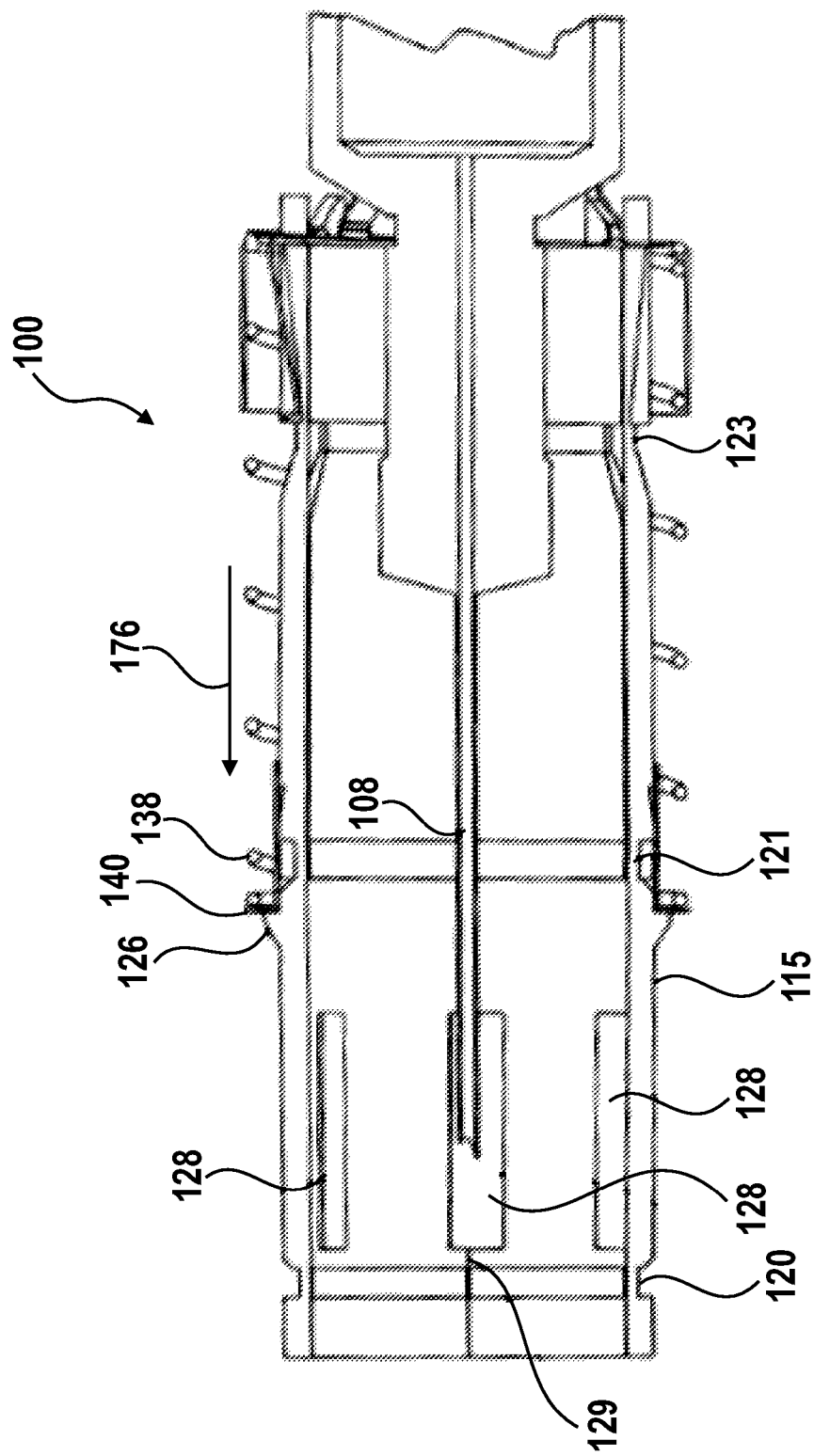
FIG. 18 depicts a side view of the syringe assembly with the folding panel needle guard fully unfolded and the spring fully extended.
Figure 19:
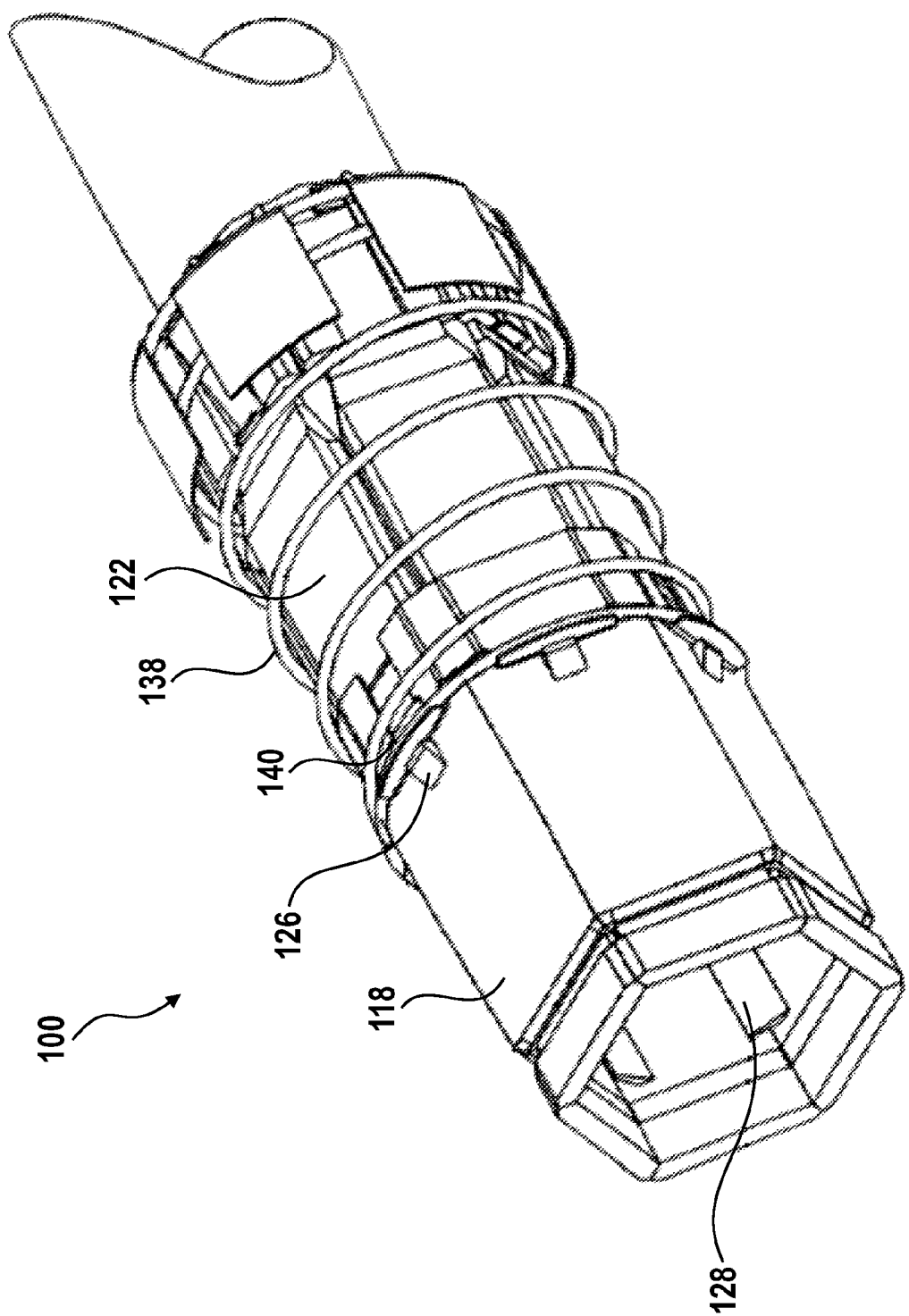
FIG. 19 depicts a partial perspective view of the syringe assembly as shown in FIG. 18.

As depicted in FIGS. 18 and 19, the folding panel needle guard 115 is fully closed, with the front panels 118 and the rear panels 122 essentially co-linear. The spring 138, having continued to resile along the spring extension path 176, has pushed the control ring 140 up against limit stops 126 on the front panels 118. The control ring 140 provides a circumferential band around the front and rear panels 118 and 122, preventing the folding and collapse, which is desirable during injection, from occurring after the needle 108 is contaminated.

As an alternative, the front panels 118 could include needle exclusion tabs 128 to shield panel gaps 129 (spaces between panels) from the needle 108, preventing any unwanted penetration from the folding panel needle guard 115 by needle 108.

Figure 20A:
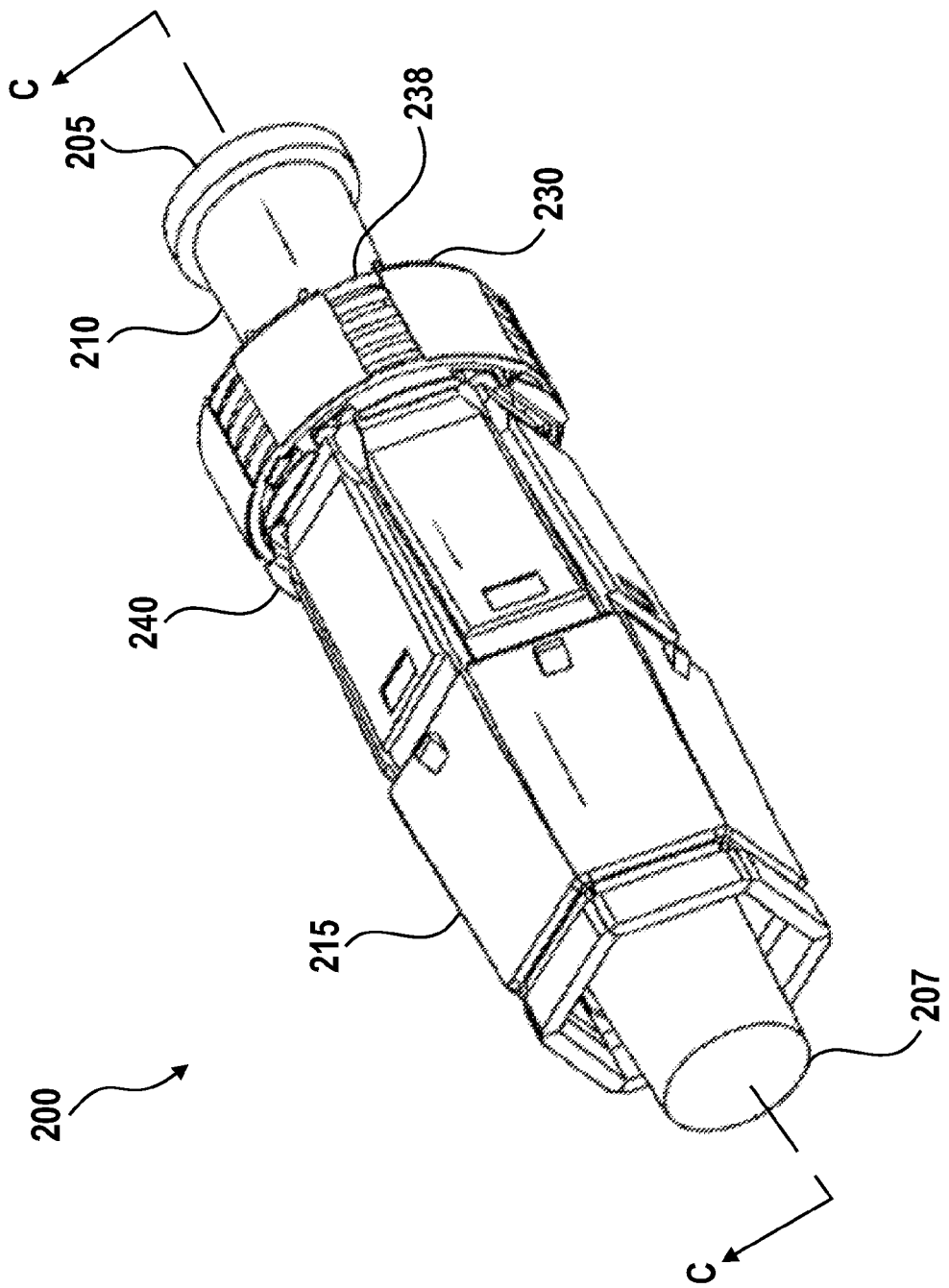
FIG. 20A depicts a perspective view of a needle assembly comprising a Luer connector, protective cap, and another embodiment of a folding panel needle guard coupled to the Luer connector.
Figure 20B:
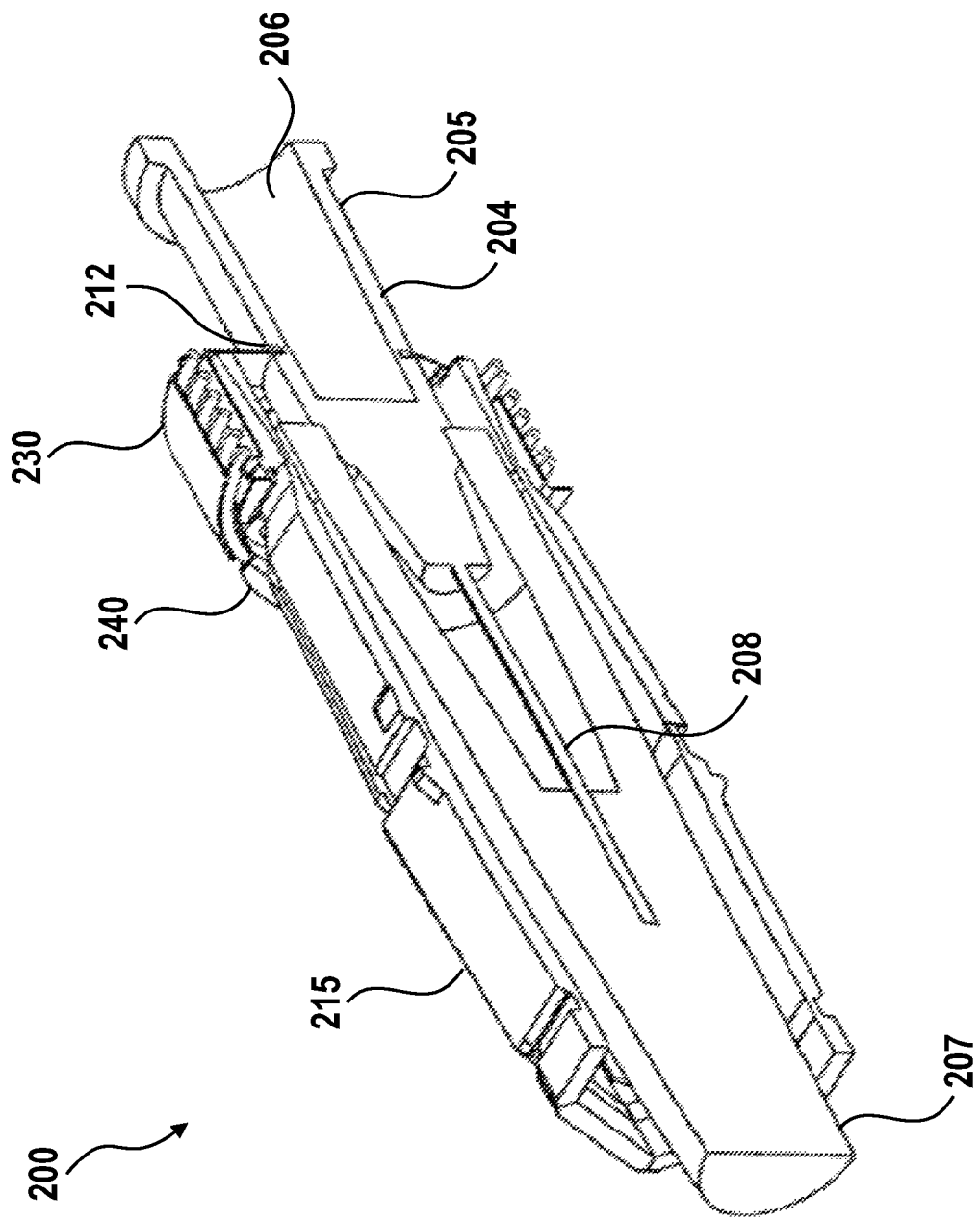
FIG. 20B depicts a sectional perspective view of the needle assembly taken along line C-C in FIG. 20A.

Turning now to FIGS. 20A-25B which show another embodiment of a folding panel needle guard 215. As depicted in FIGS. 20A and 20B, a needle assembly 200 comprises a Luer connector 205, a protective cap 207 positioned over a needle 208, and a folding panel needle guard 215. The Luer connector 205 includes an internal surface 206 and an external surface 204. The needle 208 extends from a distal end of the Luer connector 205. The folding panel needle guard 215 includes a hub 230 coupled to the Luer connector 205 at an annular recess 212 formed in the external surface 204 of the Luer connector 205. As discussed in detail below, the folding panel needle guard 215 comprises front and rear panels 218 and 222 coupled together at hinges 221, a collar 224 attached to the front panels 218 at hinges 220, a base element 225 coupled to the rear panels 222 at hinges 223, a hub 230, a control ring 240 and a spring 238 to unfold and lock the front and rear panels 218 and 222 in a co-linear needle shielded configuration.

Figure 22:
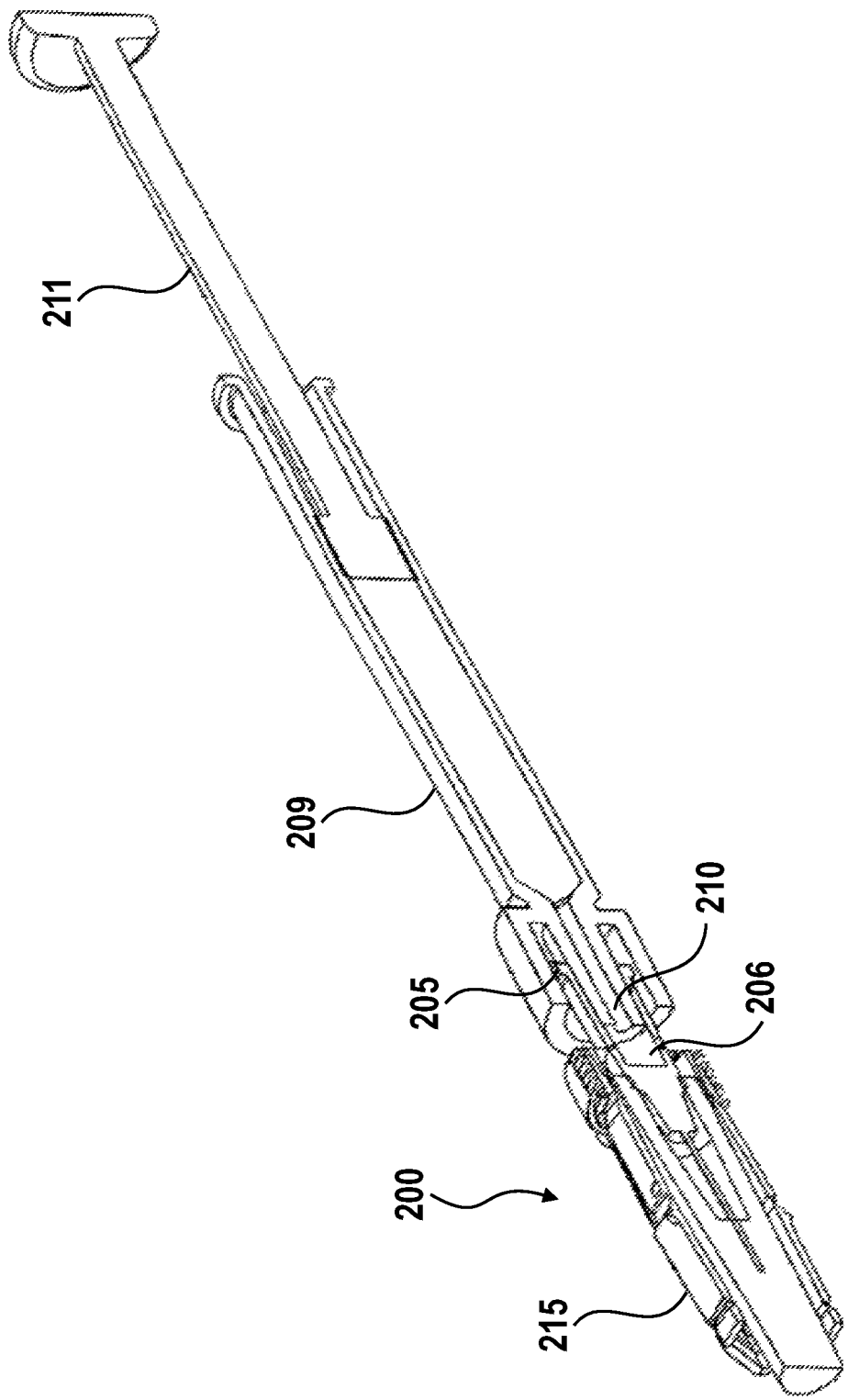
FIG. 22 depicts a sectional perspective view showing the external syringe with the external Luer connector connected to the Luer connector of the needle assembly.
Figure 23:
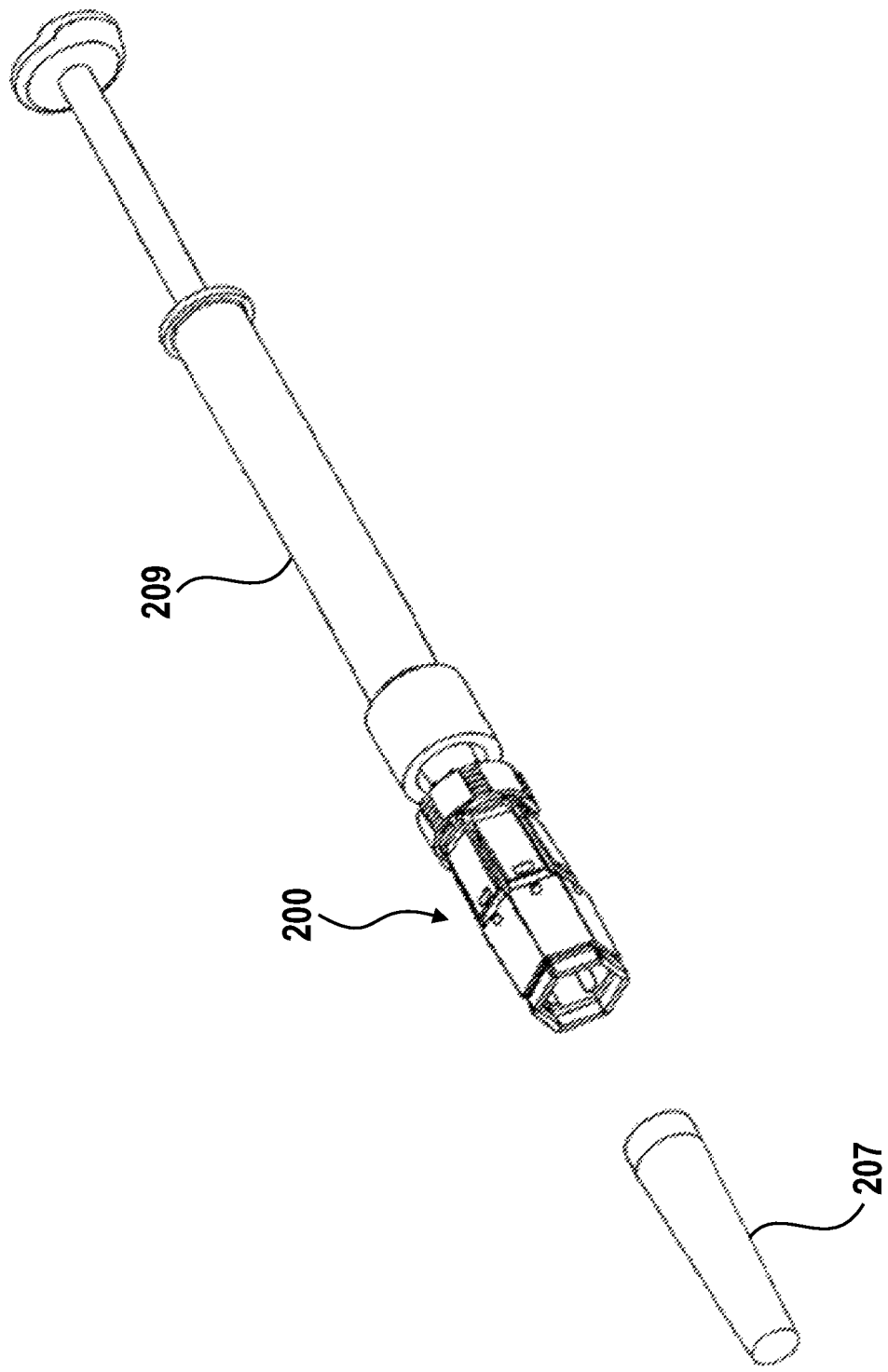
FIG. 23 depicts a partial exploded perspective view showing the external syringe with the external Luer connector connected to the Luer connector of the needle assembly with the protective cap removed.

Turning to FIG. 21, an external syringe 209 with external Luer connector 210 adapted to connect to the luer connector 205 of needle assembly 200 is shown. As depicted in FIG. 22, the needle assembly 200 is connected to the external syringe 209. Referring to FIG. 23, the needle assembly 200 is shown connected to the external syringe 209 with the protective cap 207 removed prior to injection.

Figure 24A:
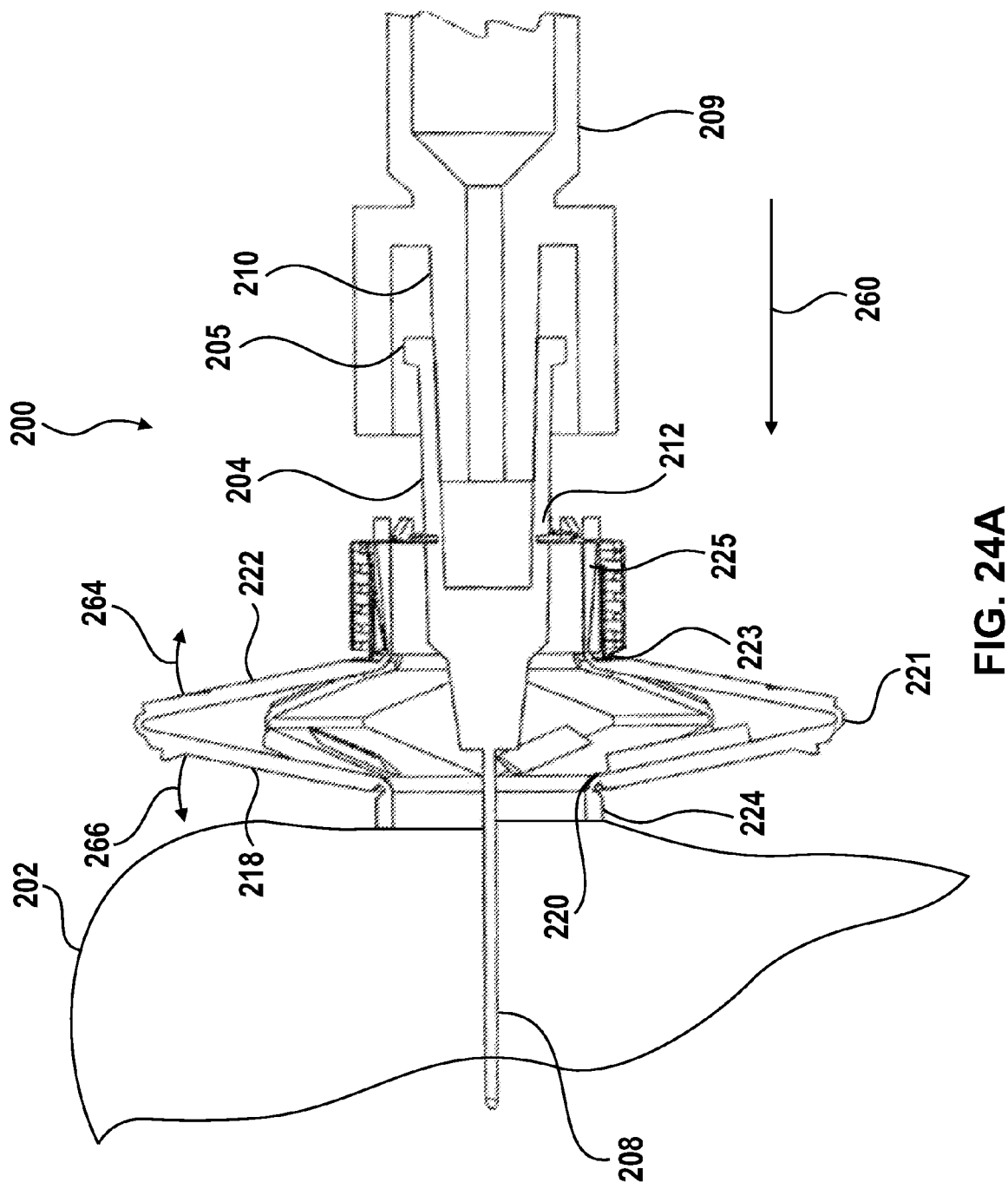
FIG. 24A depicts a partial side view of the external syringe with the external Luer connector connected to the Luer connector of the needle assembly with the needle fully imbedded into the patient and the folding panel needle guard fully collapsed.
Figure 24B:
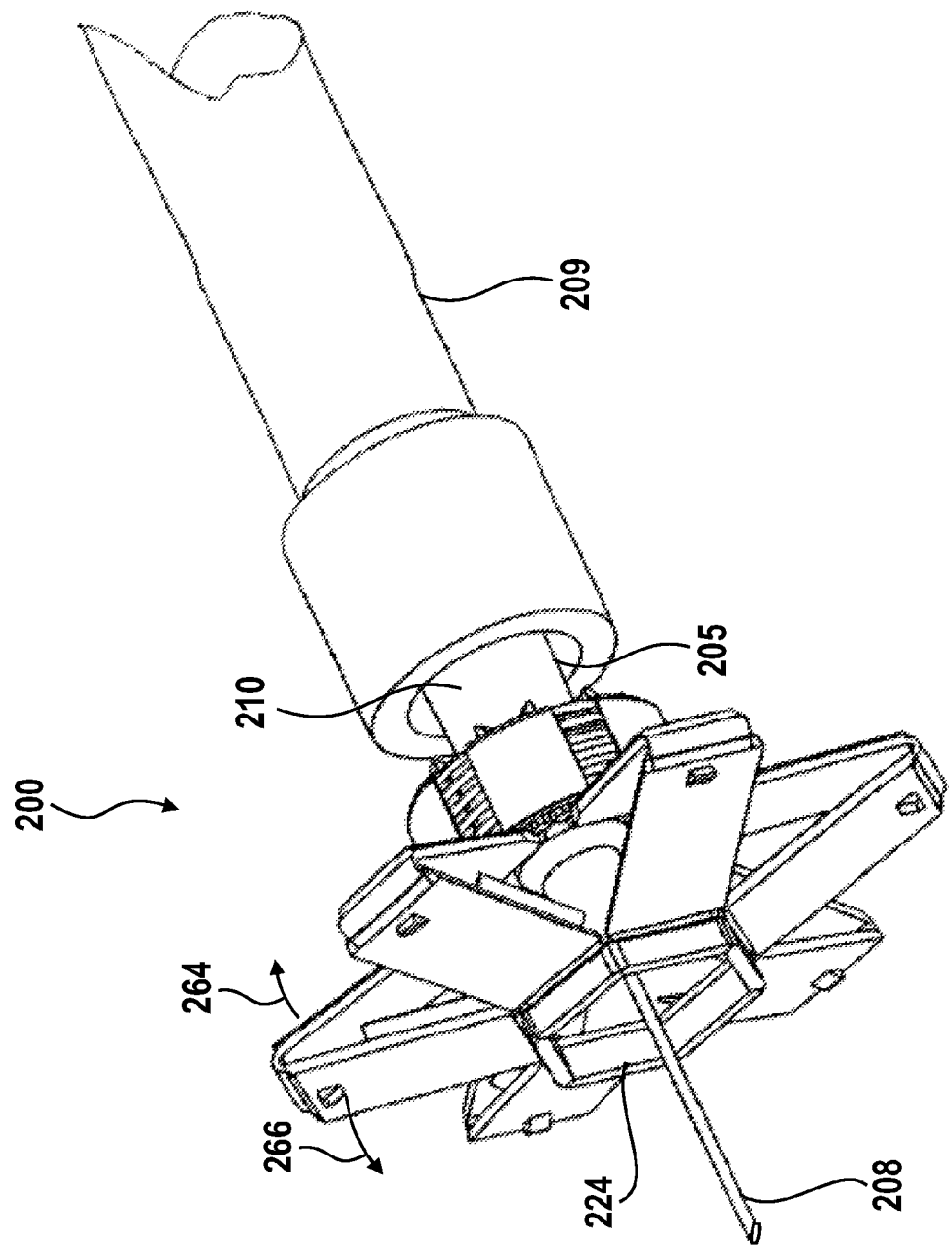
FIG. 24B depicts a partial perspective view of the external syringe with the external Luer connector connected to the Luer connector of the needle assembly with the folding panel needle guard fully collapsed as shown in FIG. 24A.

FIGS. 24A and 24B depict the needle assembly coupled to the external syringe and fully collapsed in an injection state. As depicted in FIG. 24A, the needle 208 is embedded into the patient 202. All features and functions of the syringe assembly 100 (described above) are present in the needle assembly 200 (folding panels, control ring, spring, hub, etc.). Needle assembly, connected to external syringe 209, functions exactly as the syringe assembly 100, i.e., as folding panel needle guard 215 collapses, the front panels 218 fold along front panel folding path 266, and the rear panels 222 fold along rear panel folding path 264.

Figure 25A:
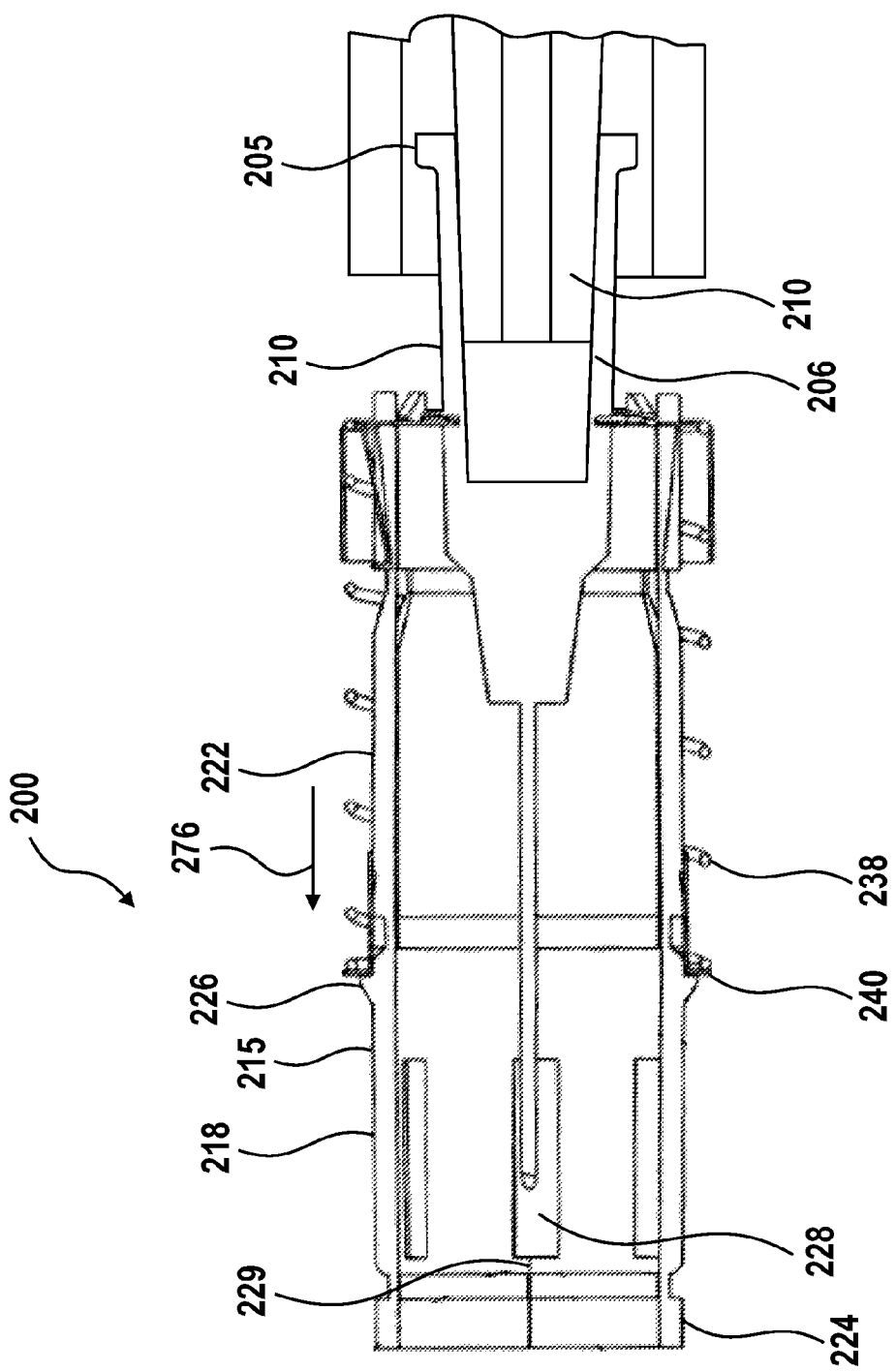
FIG. 25A depicts a partial side view of the external syringe with the external Luer connector connected to the Luer connector of the needle assembly with the folding panel needle guard fully unfolded and locked with the spring fully extended.
Figure 25B:
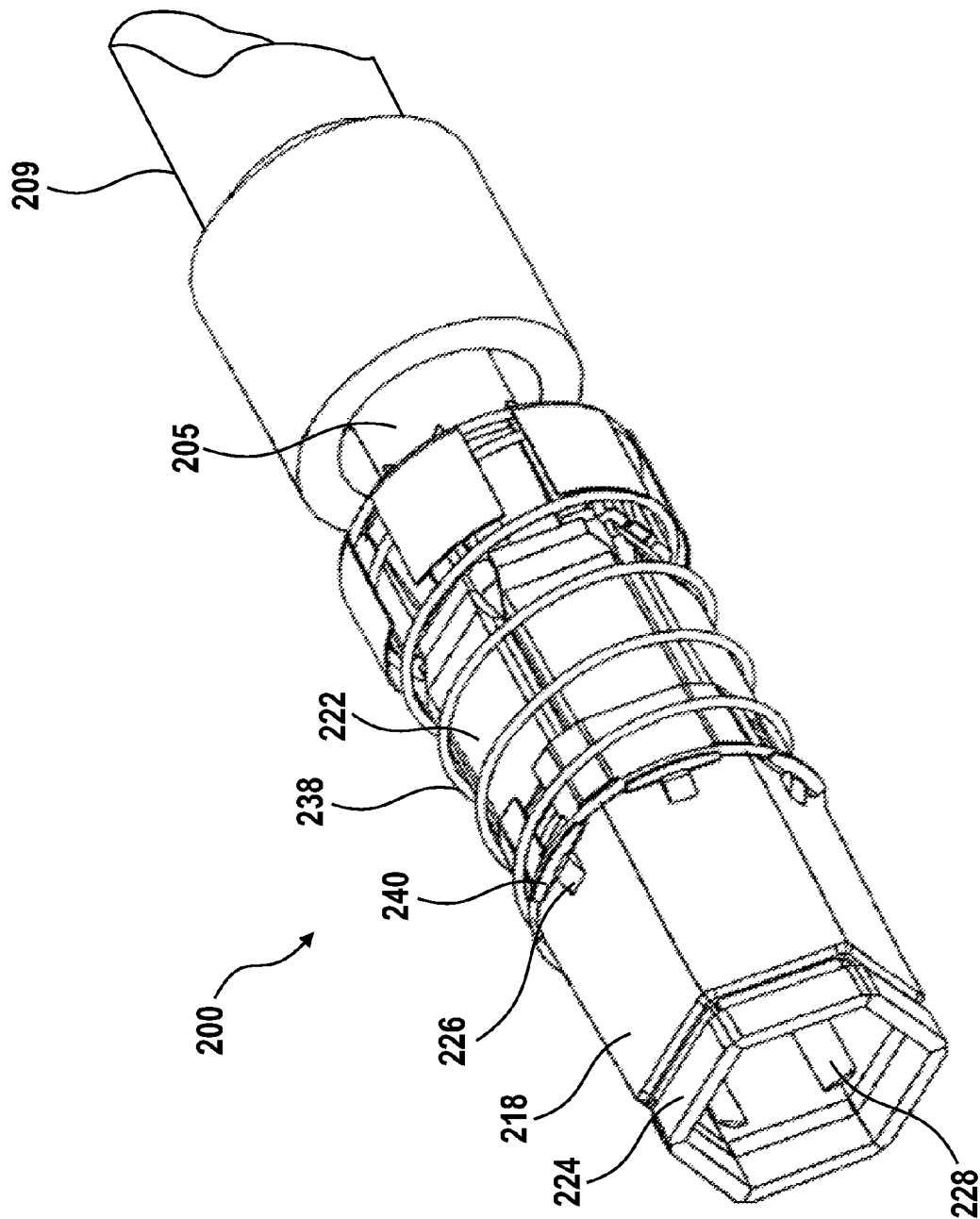
FIG. 25B depicts a partial perspective view of the external syringe with the external Luer connector connected to the Luer connector of the needle assembly with the folding panel needle guard fully unfolded and locked with the spring fully extended.

FIGS. 25A and 25B depict the needle assembly 200 in a fully locked state. The folding panel needle guard 215 is fully closed, with the front panels 218 and the rear panels 222 essentially co-linear. The spring 238, having resiled along a spring extension path 276, has pushed the control ring 240 up against limit stops 226 on the front panels. The control ring 240 provides a circumferential band around the front and rear panels 218 and 222, preventing the folding and collapse, which is desirable during injection, from occurring after the needle 208 is contaminated.

As an alternative, the front panels 218 could include needle exclusion tabs 228 to shield panel gaps 229 (spaces between panels) from the needle 208, preventing any unwanted penetration from the folding panel needle guard 215 by needle 208.

Figure 26A:
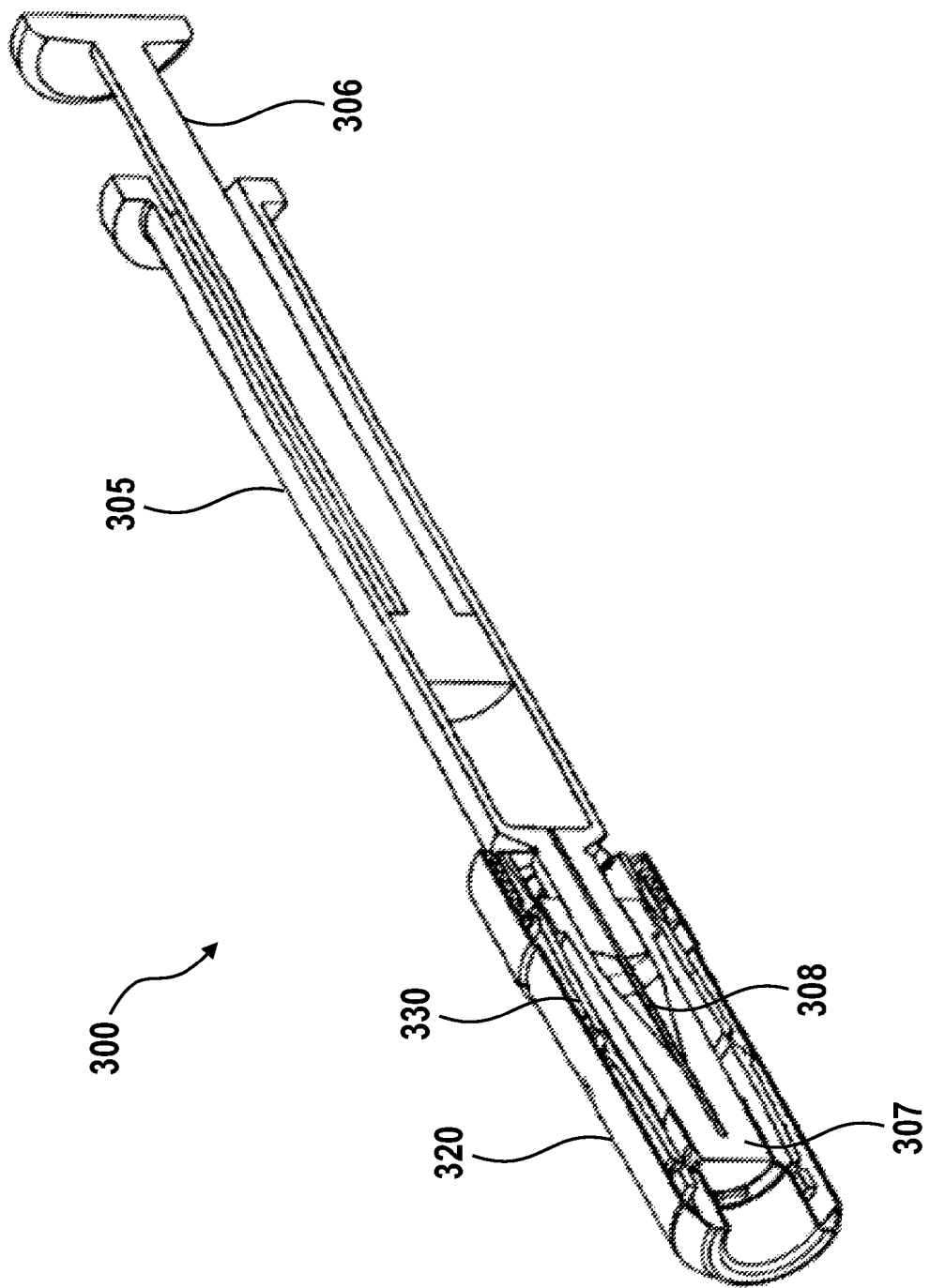
FIG. 26A depicts a sectional perspective view of an alternative protective cap structure coupled to the syringe assembly shown in FIG. 9A.
Figure 26B:
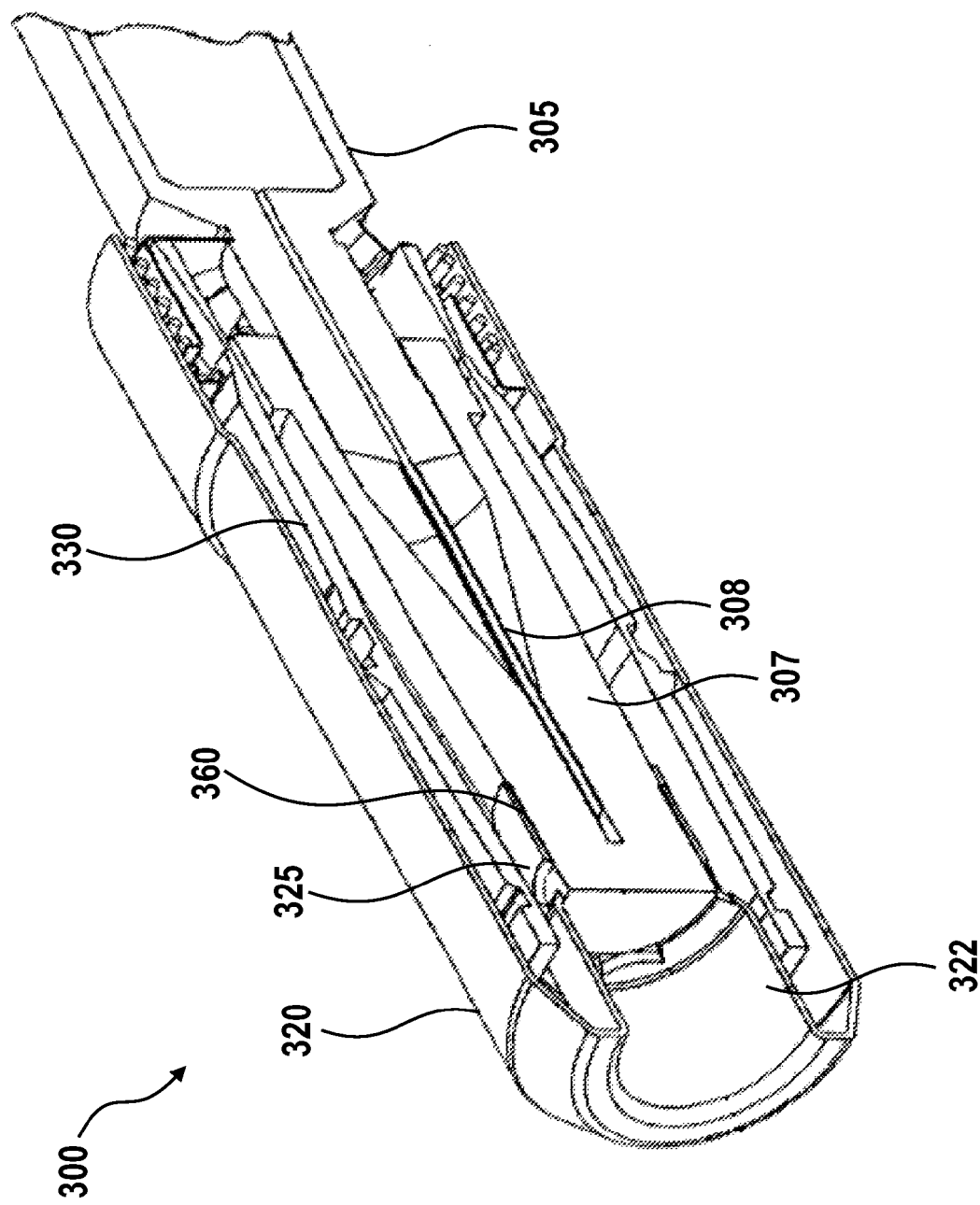
FIG. 26B depicts a detailed sectional perspective partial view of the alternative protective cap structure shown in FIG. 26A.
Figure 26C:
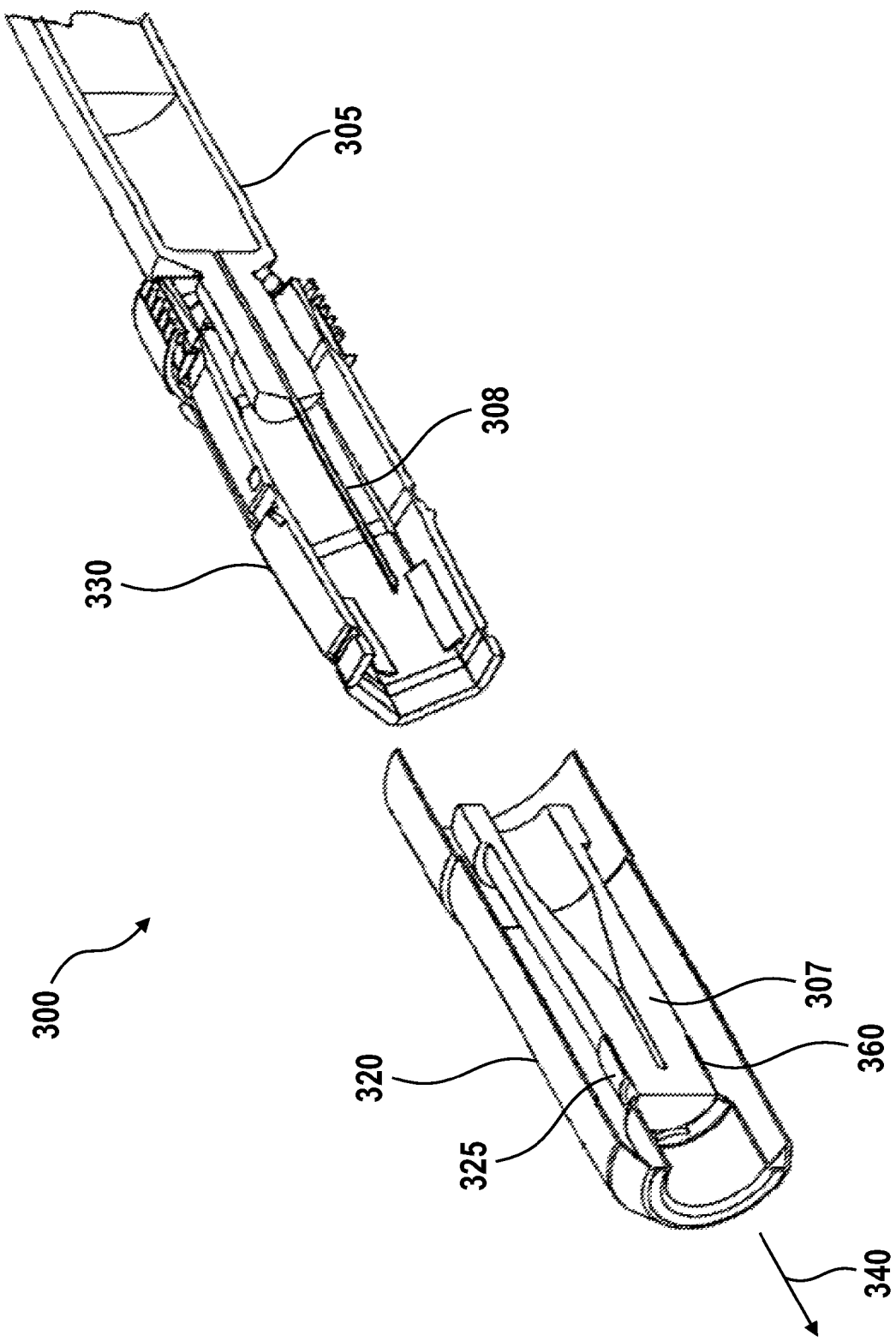
FIG. 26C depicts an exploded sectional perspective partial view of the alternative protective cap structure coupled to the syringe assembly.
Figure 27A:
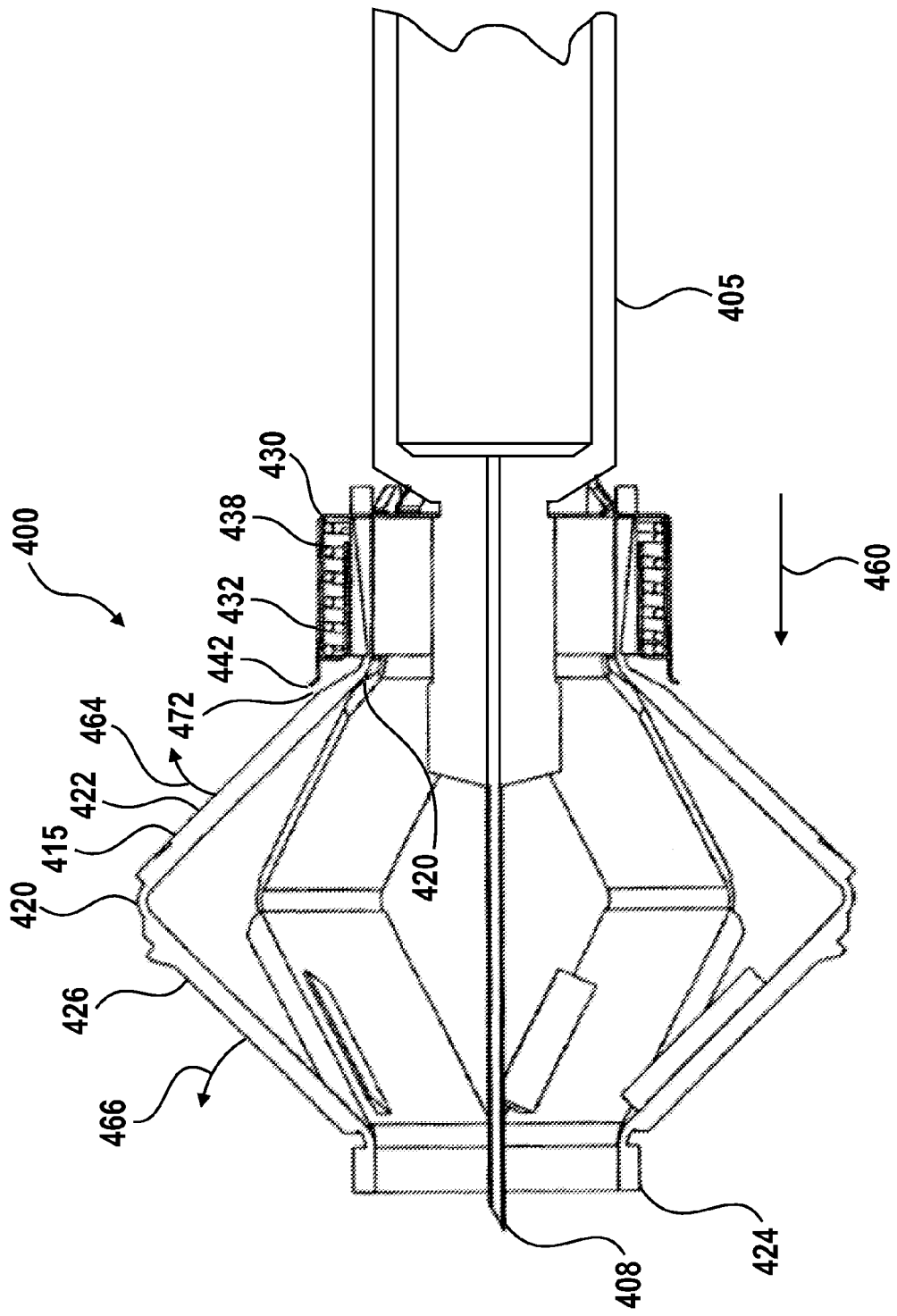
FIG. 27A depicts a partial side view of the syringe assembly of FIG. 9A with an alternative release mechanism with the folding panel needle guard partially folded.
Figure 27B:
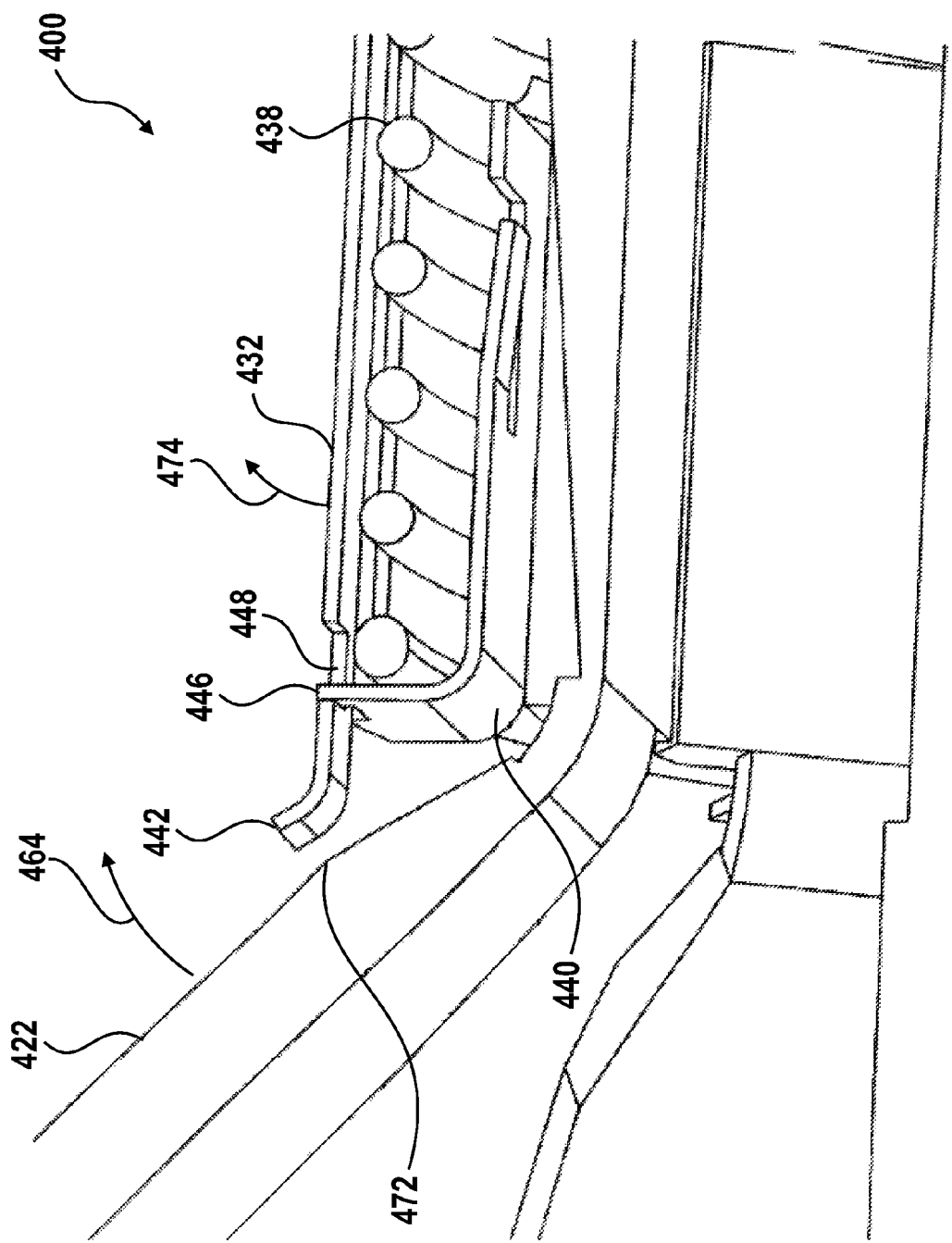
Figure 27C:
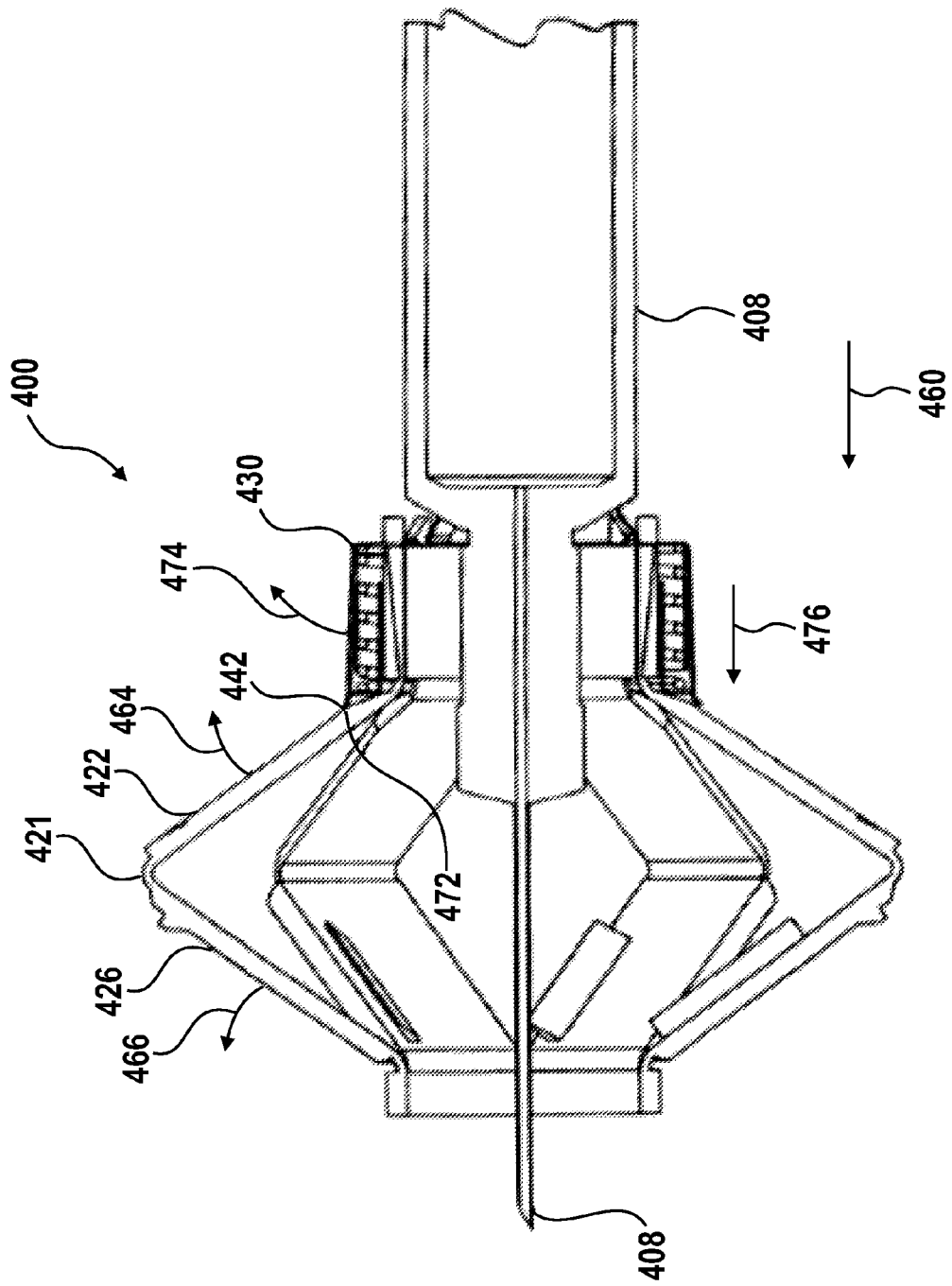
FIG. 27C depicts a partial side view of the syringe assembly with the folding panel needle guard partially folded further.
Figure 27D:
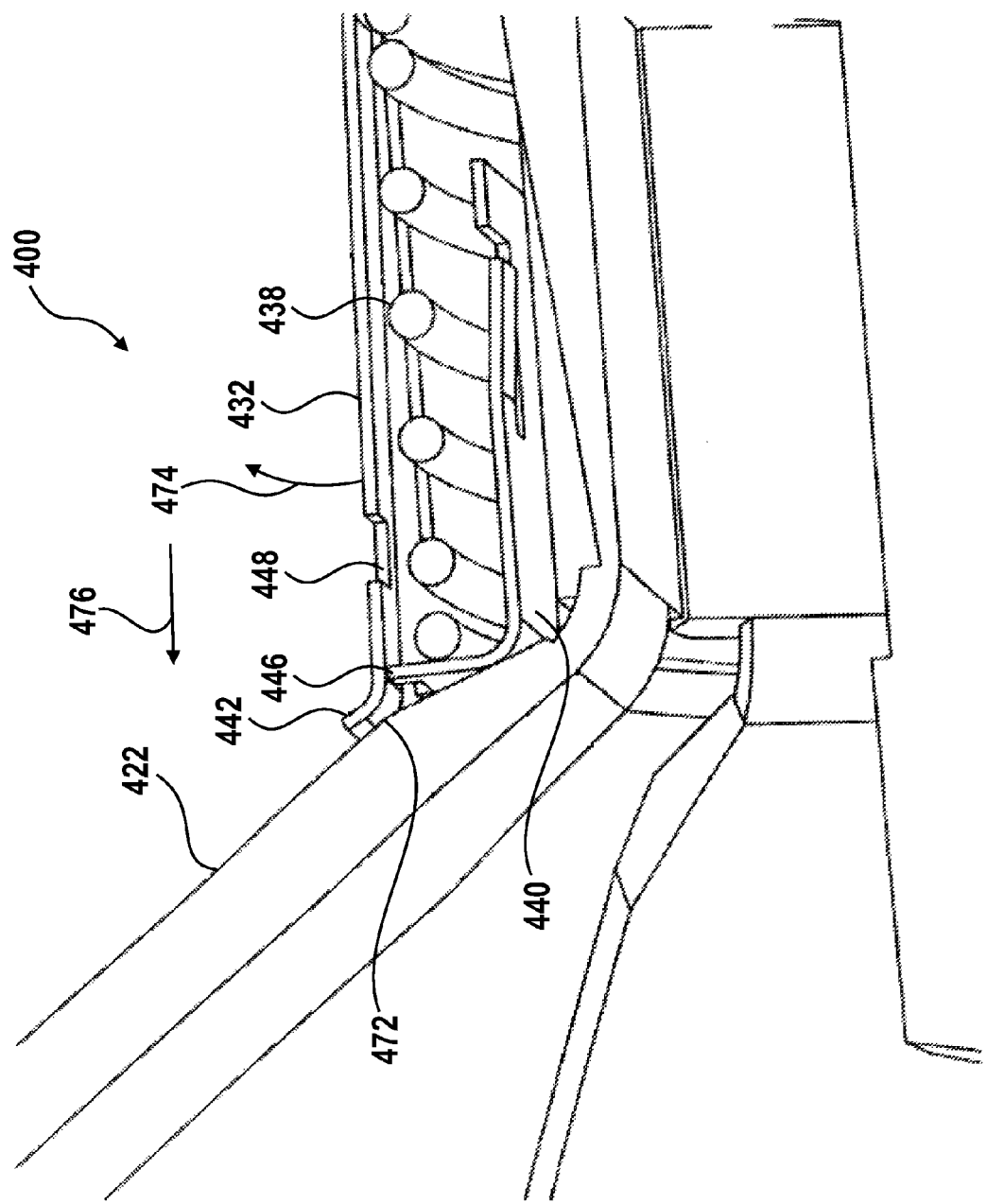
FIG. 27D depicts a detail view from FIG. 27C shown partially from underneath showing the relative positions of the control ring and latch arm as interference is eliminated.

Turning to FIGS. 26A, 26B and 26C, an alternate protective cap structure is provided. A syringe assembly 300 includes a syringe 305, a plunger 306, a folding panel needle guard 330, a protective cap 307, a cap sheath 320, and a needle 308. The cap sheath 320 covers a folding panel guard 330 to protect it from damage and premature activation. The protective cap 307 is connected to the cap sheath 320 at an interface point 360, enabling both the protective cap 307 and the cap sheath 320 to be removed together.

Referring to FIGS. 27A, 27B, 27C and 27D, an alternate activation mechanism for a folding panel needle guard is provided. A syringe assembly 400 includes a folding panel needle guard 415. As shown in previous embodiments, the syringe assembly 400 is advanced along an injection path 460, causing the folding panel needle guard 415 to collapse, thereby urging rear panels 422 to rotate approximately along a path 464.

As the rear panels 422 contact latch arm pads 442, it lifts latch arms 432 upward along a path 474. As the latch arms 432 are lifted along path 474 by contact between the rear panels 422 and latch arm pads 442, latch tabs 446 on a control ring 440 clear latch notches 448, permitting a spring 438 to resile and push the control ring 440 along a path 476. The control ring 440, driven forward by the spring 438, forces the rear panels 422 to collapse, closing the folding panel guard 415.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A needle guard comprising
a plurality of front panels circumferentially positioned about an axis,
a plurality of back panels circumferentially positioned about the axis in a first position substantially collinear with the plurality of front panels, wherein the plurality of back panels are moveably coupled to the plurality of front panels, and
a hub positioned adjacent the plurality of back panels co-axially with the plurality of front and back panels and configured to retain a spring in a compressed state, wherein the plurality of front and back panels are foldable to a second position, wherein movement of the plurality of the back panels triggers the release of the spring, wherein the spring is biased to unfold the plurality of front and back panels and return the plurality of front and back panels to the first position, wherein the hub includes a control ring operably coupled to the spring and positionable over the coupling between the plurality of front and back panels to lock the front and back panels in the first position, and wherein the hub further comprises a plurality of latch arms operably coupled to the control ring to retain the spring in compressed state, the plurality of latch arms are disengaged from the control ring to release the spring when the plurality of back panels engage the plurality of latch arms.

2. The needle guard of claim 1 wherein the spring extends over the plurality of back panels and a coupling between the plurality of front and back panels to lock the front and back panels in the first position.

3. The needle guard of claim 1 wherein the hub is couplable to one of a syringe with a needle and a needle connector couplable to a syringe.

4. The needle guard of claim 3 wherein the needle connector is a Luer connector.

5. The needle guard of claim 1 wherein the coupling between the plurality of front and back panels is a hinge.

6. The needle guard of claim 1 further comprising an annular collar flexibly coupled to the plurality of front panels.

7. The needle guard of claim 1 further comprising a trigger rib on each of the plurality of back panels, and wherein the plurality of latch arms each include a latch hook to retain the spring in a compressed state, wherein the latch arms are biased to move the latch hook out of an extension path of the spring when the trigger ribs engage the spring.

8. The needle guard of claim 1 wherein each of the plurality of latch arms each have a latch hook to retain the spring in a compressed state, wherein the latch arms are operably coupled to the control ring and biased to move the latch hook out of an extension path of the spring when the plurality of back panels engage the control ring.

9. A needle guard comprising,
a plurality of front and rear panels coupled together at a first plurality of hinges, wherein the plurality of front and rear panels is moveable from a first, substantially collinear position to a second, collapsed position,
a hub configured to retain a spring in a compressed state and comprising a control ring operably coupled to the spring and positionable over the first plurality of hinges to lock the plurality of front and rear panels in the first position, wherein movement of the plurality of the rear panels triggers the release of the spring, wherein the spring is biased to return the plurality of front and rear panels from the second, collapsed position to the first position, and
a collar attached to the front panels at a second plurality of hinges.

10. The needle guard of claim 9 further comprises a guard base element coupled to the rear panels at a third plurality of hinges.

11. The needle guard of claim 10 wherein the spring is biased to unfold the plurality of front and rear panels from the second collapsed position to the first collinear position and lock the plurality of front and rear panels in the first collinear position to shield the needle.

12. The needle guard of claim 11 wherein the hub further includes a control ring operably couplable to the spring and positionable over the first plurality of hinges to lock the plurality of front and back panels in the first collinear position.

13. The needle guard of claim 12 wherein the hub further comprises a plurality of latch arms each with a latch hook to retain the spring in compressed state, wherein the latch arms are operably coupled to the control ring and biased to move the latch hook out of an extension path of the spring when the plurality of back panels engage the control ring.

14. The needle guard of claim 11 further comprising a trigger rib on each of the plurality of back panels, and wherein the hub further comprises a plurality of latch arms each with a latch hook to retain the spring in a compressed state, wherein the latch arms are biased to move the latch hook out of an extension path of the spring when the trigger ribs engage the spring.

15. A needle guard comprising,
- a plurality of front and rear panels coupled together at a first plurality of hinges, wherein the plurality of front and rear panels is moveable from a first, substantially collinear position to a second, collapsed position,
- a collar attached to the front panels at a second plurality of hinges,
- a guard base element coupled to the rear panels at a third plurality of hinges,
- a spring that is biased to unfold the plurality of front and rear panels from the second collapsed position to the first collinear position and lock the plurality of front and rear panels in the first collinear position to shield the needle, and
- a hub to retain the spring in a compressed state, wherein the hub includes a control ring operably couplable to the spring and positionable over the first plurality of hinges to lock the plurality of front and back panels in the first collinear position, and wherein the hub further comprises a plurality of latch arms operably coupled to the control ring to retain the spring in a compressed state, the plurality of latch arms are disengaged from the control ring to release the spring when the plurality of back panels engage the plurality of latch arms.

* * * * *